(12) United States Patent
Katzman et al.

(10) Patent No.: US 11,253,409 B2
(45) Date of Patent: Feb. 22, 2022

(54) SYSTEMS AND METHODS FOR MOBILE DENTITION SCANNING

(71) Applicant: SDC U.S. SmilePay SPV, Nashville, TN (US)

(72) Inventors: Jordan Katzman, Nashville, TN (US); Alex Fenkell, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 16/577,912

(22) Filed: Sep. 20, 2019

(65) Prior Publication Data
US 2020/0035353 A1 Jan. 30, 2020

Related U.S. Application Data

(63) Continuation-in-part of application No. 16/130,762, filed on Sep. 13, 2018, which is a continuation-in-part of application No. 15/725,430, filed on Oct. 5, 2017.
(Continued)

(51) Int. Cl.
*A61G 3/00* (2006.01)
*G16H 40/20* (2018.01)
(Continued)

(52) U.S. Cl.
CPC .............. *A61G 3/001* (2013.01); *A61B 6/145* (2013.01); *A61C 7/002* (2013.01); *A61C 9/0053* (2013.01);
(Continued)

(58) Field of Classification Search
CPC ....... A61B 6/145; A61C 7/002; A61C 9/0053; A61G 3/001; A61G 3/003; A61G 10/00; A61G 15/002; A61G 15/14
(Continued)

(56) References Cited

U.S. PATENT DOCUMENTS

| 4,003,132 A | 1/1977 | Deck |
| 4,763,791 A | 8/1988 | Halverson et al. |

(Continued)

FOREIGN PATENT DOCUMENTS

| AU | 2015100268 | 5/2015 |
| CN | 204472650 | 7/2015 |

(Continued)

OTHER PUBLICATIONS

SwankySmiles advertisement from Feb. 8, 2019; located at www.swankysmiles.com (click on Watch the Video). (Year: 2019).*
(Continued)

*Primary Examiner* — Jason S Daniels
(74) *Attorney, Agent, or Firm* — Foley & Lardner LLP

(57) ABSTRACT

Systems and methods relate to a mobile intraoral scanning site. The mobile intraoral scanning site includes a vehicle and one or more three-dimensional intraoral scanners provided on the vehicle and configured to perform intraoral dentition scans of users on the vehicle. The vehicle can include at least two compartments configured to be used as scan stations for performing the intraoral dentitions scans of the users on the vehicle. The vehicle can be retrofitted to be used for the mobile intraoral scanning site. The one or more three-dimensional intraoral scanners can be wall-mounted on the vehicle. The vehicle can be provided with an internet connection such that the intraoral dentition scans are uploaded to a cloud server via the internet connection. Messages can be sent to a plurality of individuals inviting the plurality of individuals to schedule an appointment to receive an intraoral dentition scan at the vehicle.

21 Claims, 14 Drawing Sheets

Related U.S. Application Data

(60) Provisional application No. 62/660,141, filed on Apr. 19, 2018, provisional application No. 62/522,847, filed on Jun. 21, 2017.

(51) Int. Cl.
  *G06Q 10/02* (2012.01)
  *G06Q 10/10* (2012.01)
  *G08G 1/00* (2006.01)
  *A61B 6/14* (2006.01)
  *A61C 7/00* (2006.01)
  *A61C 9/00* (2006.01)

(52) U.S. Cl.
  CPC .............. *A61G 3/003* (2013.01); *G06Q 10/02* (2013.01); *G06Q 10/1095* (2013.01); *G08G 1/202* (2013.01); *G16H 40/20* (2018.01)

(58) Field of Classification Search
  USPC .......................................... 296/24.38, 24.39
  See application file for complete search history.

(56) References Cited

U.S. PATENT DOCUMENTS

| | | |
|---|---|---|
| 5,093,901 A | 3/1992 | Cree et al. |
| 5,190,168 A | 3/1993 | French et al. |
| 5,385,155 A | 1/1995 | Kittelsen et al. |
| 5,816,255 A | 10/1998 | Fishman et al. |
| 5,882,192 A | 3/1999 | Bergersen |
| 5,975,893 A | 11/1999 | Chishti et al. |
| 6,227,851 B1 | 5/2001 | Chishti et al. |
| 6,394,801 B2 | 5/2002 | Chishti et al. |
| 6,450,807 B1 | 9/2002 | Chishti et al. |
| 6,488,499 B1 | 12/2002 | Miller |
| 6,582,225 B1 | 6/2003 | Bergersen |
| 6,632,089 B2 | 10/2003 | Rubbert et al. |
| 6,699,037 B2 | 3/2004 | Chishti et al. |
| 6,732,103 B1 | 5/2004 | Strick et al. |
| 6,761,560 B2 | 7/2004 | Miller |
| 7,037,108 B2 | 5/2006 | Chishti et al. |
| 7,077,647 B2 | 7/2006 | Choi et al. |
| 7,156,661 B2 | 1/2007 | Choi et al. |
| 7,188,073 B1 | 3/2007 | Tam et al. |
| 7,192,275 B2 | 3/2007 | Miller |
| 7,383,198 B1 | 6/2008 | Sepe |
| 7,467,022 B2 | 12/2008 | Bhagwat et al. |
| 7,523,044 B2 | 4/2009 | Rosenblood |
| 7,578,674 B2 | 8/2009 | Chishti et al. |
| 7,597,245 B1 | 10/2009 | Tillery |
| 7,716,062 B2 | 5/2010 | Bergersen |
| 7,738,989 B2 | 6/2010 | Taub et al. |
| 7,904,307 B2 | 3/2011 | Abolfathi et al. |
| 7,916,900 B2 | 3/2011 | Lanier |
| 7,967,145 B2 | 6/2011 | Tchouangang |
| 8,015,049 B1 | 9/2011 | Tam et al. |
| 8,075,306 B2 | 12/2011 | Kitching et al. |
| 8,087,932 B2 | 1/2012 | Liu |
| 8,092,215 B2 | 1/2012 | Stone-Collonge et al. |
| 8,145,340 B2 | 3/2012 | Taub et al. |
| 8,287,275 B2 | 10/2012 | Knutson |
| 8,303,301 B2 | 11/2012 | Bergersen |
| 8,562,338 B2 | 10/2013 | Kitching et al. |
| 8,577,493 B2 | 11/2013 | Taub et al. |
| 8,591,225 B2 | 11/2013 | Wu et al. |
| 8,636,510 B2 | 1/2014 | Kitching et al. |
| 8,651,859 B2 | 2/2014 | Chishti et al. |
| 8,731,280 B2 | 5/2014 | Kuo et al. |
| 8,740,614 B2 | 6/2014 | Wen et al. |
| 8,765,031 B2 | 7/2014 | Li et al. |
| 8,899,978 B2 | 12/2014 | Kitching et al. |
| 9,017,072 B2 | 4/2015 | Kitching et al. |
| 9,107,722 B2 | 8/2015 | Matov et al. |
| 9,168,113 B2 | 10/2015 | Wu et al. |
| 9,256,962 B2 | 2/2016 | Berry et al. |
| 9,364,297 B2 | 6/2016 | Kitching et al. |
| D764,061 S | 8/2016 | Furdui-Carr |
| 9,655,693 B2 | 5/2017 | Li et al. |
| 9,715,753 B2 | 7/2017 | Berry et al. |
| 9,757,065 B1 | 9/2017 | Suri et al. |
| 9,855,123 B2 | 1/2018 | Wolgin |
| 9,922,170 B2 | 3/2018 | Trosien et al. |
| 10,052,174 B2 | 8/2018 | Kitching et al. |
| 10,085,823 B2 | 10/2018 | Cao et al. |
| 10,136,972 B2 | 11/2018 | Sabina et al. |
| 10,231,801 B2 | 3/2019 | Korytov et al. |
| 10,342,638 B2 | 7/2019 | Kitching et al. |
| 10,383,705 B2 | 8/2019 | Shanjani et al. |
| 10,504,386 B2 | 12/2019 | Levin et al. |
| 10,595,966 B2 | 3/2020 | Carrier et al. |
| 2001/0027481 A1 | 10/2001 | Whyel |
| 2002/0007290 A1 | 1/2002 | Gottlieb |
| 2002/0014357 A1 | 2/2002 | Hammonds |
| 2002/0028418 A1 | 3/2002 | Farag et al. |
| 2002/0029161 A1 | 3/2002 | Brodersen et al. |
| 2002/0116232 A1 | 8/2002 | Rapp et al. |
| 2002/0131565 A1 | 9/2002 | Scheuring et al. |
| 2002/0143574 A1 | 10/2002 | Karras et al. |
| 2002/0188478 A1 | 12/2002 | Breeland et al. |
| 2003/0138752 A1 | 7/2003 | Bergersen |
| 2003/0207227 A1 | 11/2003 | Abolfathi |
| 2003/0225594 A1 | 12/2003 | Bergersen |
| 2004/0073611 A1 | 4/2004 | Atwood |
| 2004/0091835 A1 | 5/2004 | Roetzer |
| 2004/0152036 A1 | 8/2004 | Abolfathi |
| 2004/0185415 A1 | 9/2004 | Ghim |
| 2004/0197728 A1 | 10/2004 | Abolfathi et al. |
| 2004/0250359 A1 | 12/2004 | Spivey |
| 2005/0159986 A1 | 7/2005 | Breeland et al. |
| 2005/0182654 A1 | 8/2005 | Adolfathi et al. |
| 2006/0026051 A1 | 2/2006 | Rose |
| 2006/0040230 A1 | 2/2006 | Blanding et al. |
| 2006/0057541 A1 | 3/2006 | Kahwaty |
| 2006/0064329 A1 | 3/2006 | Adolfathi et al. |
| 2006/0093982 A1 | 5/2006 | Wen |
| 2006/0141416 A1 | 6/2006 | Knutson |
| 2006/0154198 A1 | 7/2006 | Durdin et al. |
| 2006/0167724 A1 | 7/2006 | Petersen et al. |
| 2006/0173708 A1 | 8/2006 | Vining et al. |
| 2006/0275731 A1 | 12/2006 | Wen et al. |
| 2006/0275736 A1 | 12/2006 | Wen et al. |
| 2007/0005406 A1 | 1/2007 | Assadian et al. |
| 2007/0036320 A1 | 2/2007 | Mandalia et al. |
| 2007/0037116 A1 | 2/2007 | Knutson |
| 2007/0061166 A1 | 3/2007 | Ramasubramanian et al. |
| 2007/0102946 A1* | 5/2007 | Blackwell .............. A61G 3/001 296/24.38 |
| 2007/0128574 A1 | 6/2007 | Kuo et al. |
| 2007/0134613 A1 | 6/2007 | Kuo et al. |
| 2007/0238065 A1 | 10/2007 | Sherwood et al. |
| 2008/0059227 A1 | 3/2008 | Clapp |
| 2008/0159798 A1 | 7/2008 | Culp et al. |
| 2008/0206705 A1 | 8/2008 | Kaza et al. |
| 2008/0305454 A1 | 12/2008 | Kitching et al. |
| 2008/0306724 A1 | 12/2008 | Kitching et al. |
| 2008/0308450 A1 | 12/2008 | Tchouangang |
| 2009/0061381 A1 | 3/2009 | Durdin et al. |
| 2009/0081604 A1 | 3/2009 | Fisher |
| 2009/0081611 A1 | 3/2009 | Hines et al. |
| 2009/0136893 A1 | 5/2009 | Zegarelli |
| 2009/0215003 A1 | 8/2009 | Swain et al. |
| 2010/0036682 A1 | 2/2010 | Trosien et al. |
| 2010/0068676 A1 | 3/2010 | Mason et al. |
| 2010/0070297 A1 | 3/2010 | Kharraz Tavakol et al. |
| 2010/0082391 A1 | 4/2010 | Soerensen et al. |
| 2010/0105011 A1 | 4/2010 | Karkar et al. |
| 2010/0145754 A1 | 6/2010 | Rahman |
| 2010/0153162 A1 | 6/2010 | Tam et al. |
| 2010/0179854 A1 | 7/2010 | Shafer et al. |
| 2011/0084093 A1 | 4/2011 | Nehren et al. |
| 2011/0106557 A1 | 5/2011 | Gazula |
| 2011/0161249 A1 | 6/2011 | Whitehouse |
| 2011/0183293 A1 | 7/2011 | Tchouangang |
| 2011/0215933 A1 | 9/2011 | Darling et al. |

(56) References Cited

U.S. PATENT DOCUMENTS

| | | |
|---|---|---|
| 2012/0065985 A1 | 3/2012 | Royal et al. |
| 2012/0083549 A1 | 4/2012 | Kamohara et al. |
| 2012/0267811 A1 | 10/2012 | Weitzman |
| 2012/0330677 A1 | 12/2012 | Velimesis |
| 2013/0028617 A1 | 1/2013 | Fukuoka et al. |
| 2013/0035955 A1 | 2/2013 | Torres |
| 2013/0087157 A1 | 4/2013 | Hawkins et al. |
| 2013/0089828 A1 | 4/2013 | Borovinskih et al. |
| 2013/0122448 A1 | 5/2013 | Kitching |
| 2013/0230300 A1 | 9/2013 | Saleh et al. |
| 2013/0286174 A1 | 10/2013 | Urakade |
| 2014/0122100 A1 | 5/2014 | Fillmore |
| 2014/0199653 A1 | 7/2014 | Kurthy |
| 2014/0249878 A1 | 9/2014 | Kaufman |
| 2014/0278679 A1 | 9/2014 | Navani et al. |
| 2014/0315153 A1 | 10/2014 | Kitching et al. |
| 2014/0330577 A1 | 11/2014 | Herman et al. |
| 2014/0356798 A1 | 12/2014 | Parker |
| 2014/0379356 A1 | 12/2014 | Sachdeva et al. |
| 2015/0010879 A1 | 1/2015 | Kurthy |
| 2015/0202025 A1 | 7/2015 | Kaza et al. |
| 2015/0205921 A1 | 7/2015 | Dick et al. |
| 2015/0220887 A1 | 8/2015 | Peres et al. |
| 2015/0238283 A1 | 8/2015 | Tanugula et al. |
| 2015/0257859 A1 | 9/2015 | Akl |
| 2015/0310387 A1 | 10/2015 | Friedman et al. |
| 2016/0012182 A1 | 1/2016 | Golay |
| 2016/0034871 A1 | 2/2016 | Vargas et al. |
| 2016/0132893 A1 | 5/2016 | Bisges et al. |
| 2016/0158627 A1 | 6/2016 | Layzell |
| 2016/0253464 A1 | 9/2016 | Balwani et al. |
| 2016/0256240 A1 | 9/2016 | Shivapuja et al. |
| 2016/0263732 A1 | 9/2016 | Lourenco et al. |
| 2016/0287198 A1 | 10/2016 | Abramovich et al. |
| 2016/0317264 A1 | 11/2016 | Derraugh et al. |
| 2017/0010252 A1 | 1/2017 | Bearup et al. |
| 2017/0020642 A1 | 1/2017 | Mah |
| 2017/0039423 A1 | 2/2017 | Cork et al. |
| 2017/0046486 A1 | 2/2017 | Cunningham |
| 2017/0156830 A1 | 6/2017 | Wallace |
| 2017/0165040 A1 | 6/2017 | Wolgin |
| 2017/0231721 A1 | 8/2017 | Akeel et al. |
| 2017/0239018 A1 | 8/2017 | Kim |
| 2017/0281313 A1 | 10/2017 | Kim |
| 2017/0340414 A1 | 11/2017 | Janzadeh et al. |
| 2017/0347953 A1 | 12/2017 | Suri et al. |
| 2018/0014914 A1 | 1/2018 | Raghavan et al. |
| 2018/0110589 A1 | 4/2018 | Gao |
| 2018/0125610 A1 | 5/2018 | Carrier et al. |
| 2018/0206940 A1 | 7/2018 | Kopelman et al. |
| 2018/0228359 A1 | 8/2018 | Meyer et al. |
| 2018/0263731 A1 | 9/2018 | Pokotilov et al. |
| 2018/0263733 A1 | 9/2018 | Pokotilov et al. |
| 2018/0285801 A1 | 10/2018 | Alde et al. |
| 2018/0303580 A1 | 10/2018 | Salah et al. |
| 2018/0368943 A1 | 12/2018 | Katzman et al. |
| 2018/0368953 A1 | 12/2018 | Katzman et al. |
| 2018/0368954 A1 | 12/2018 | Katzman et al. |
| 2019/0026598 A1 | 1/2019 | Salah et al. |
| 2019/0038383 A1 | 2/2019 | Webber et al. |
| 2019/0083219 A1 | 3/2019 | Sharer |
| 2019/0252066 A1 | 8/2019 | Katzman et al. |
| 2019/0388188 A1 | 12/2019 | Kaza et al. |
| 2020/0081413 A1* | 3/2020 | Georg ............... G05B 19/4099 |
| 2020/0289238 A1* | 9/2020 | Levine ............... A61C 9/0053 |
| 2020/0401976 A1 | 12/2020 | Nelson et al. |

FOREIGN PATENT DOCUMENTS

| | | |
|---|---|---|
| EP | 2 425 734 | 3/2012 |
| WO | WO-2015/054746 | 4/2015 |

OTHER PUBLICATIONS

Screen grab from google showing SwankySMiles advertisemnt and post date of Feb. 8, 2019. (Year: 2019).*

NPL document Candid Co.; located at https://www.candidco.com/how-it-works/; as existed on Sep. 21, 2018; located using the INternet Archive WayBack Machine. (Year: 2018).*

Screen grab of https://www.candidco.com/how-it-works/ showing full virtual teledenstry—not in person. (Year: 2018).*

SmileCareClub promo video uploaded on Jun. 6, 2014 https://www.youtube.com/watch?v=h7x8BwWXUsk.

"203221—SmileCareClub" video, uploaded to YouTube on Jun. 10, 2014, https://www.youtube.com/watch?v=B43vT_1GnR0.

"Affordable Clear Braces—Smile Care Club" video, uploaded to YouTube on Mar. 30, 2015, https://www.youtube.com/watch?v=Qk-VhbH1RVM.

"Clear Braces . . . At Home??! Review—Before & After—Cost" video, uploaded to YouTube on Oct. 7, 2014, https://www.youtube.com/watch?v=9wrwhRTPjtk&t.

"Invisalign Manufacturing Process English" video, uploaded to YouTube on Apr. 7, 2014, https://www.youtube.com/watch?v=vsR0_wTR2a8.

"Smile Care Club Unboxing, Review, Tutorial" video, uploaded to YouTube on May 1, 2015, https://www.youtube.com/watch?v=p7Y5fMRnJWE.

"Speak Out Game—Ellen Show with Khloe Kardashian and Kevin Hart", uploaded to YouTube on Oct. 11, 2016, https://www.youtube.com/watch?v=RDILAiBFRLY.

"Step 1! Working on my Smile . . . Smile Care Club" video, uploaded to YouTube on Jan. 4, 2015, https://www.youtube.com/watch?v=T_F3Xt4Og7w.

International Search Report and Written Opinion for International Application No. PCT/US2018/038459, dated Oct. 22, 2018, 13 pages.

Smile Care Club, "Impression Kit", Jul. 21, 2014, available for retrieval at URL https://vimeo.com/wmvproductions/review/115725718/28854a7f49.

Smile Care Club, "Impressions—New Box", 2015,available for retrieval at URL https://vimeo.com/wmvproductions/review/137176701/d45be82d56.

Smile Care Club, "Impressions—Old Box", 2015,available for retrieval at URL https://vimeo.com/wmvproductions/review/137176599/0b8020929d.

Smile Care Club, "Impressions ReEdit", 2016,available for retrieval at URL https://vimeo.com/wmvproductions/review/168249998/0b75310374.

Smile Care Club, "Impressions", 2015,available for retrieval at URL https://vimeo.com/wmvproductions/review/136533463/1a8515abf5.

Smile Care Club, "Promo", 2014, available for retrieval at URL https://vimeo.com/wmvproductions/review/115725719/9c8235cdf2.

Smile Direct Club Impression Guide (available online Nov. 14, 2016, https://www.sharperimage.com/si/pdf/manuals/203221.pdf accessed Sep. 3, 2019 (Year: 2016), 24 pages.

Smile Direct Club Vimeo online video uploaded publicly on Mar. 2, 2016 (https://vimeo.com/157450883, pdf attachment of screen captures published online (Year: 2016) accessed and recorded on Dec. 13, 2018.

SmileDirectClub, "What's a Smile Shop?", https://blog.smiledirectclub.com/what-is-smiledirectclub-smileshop/ Apr. 6, 2017, 7 pages.

"203221—SmileCareClub" video, uploaded to YouTube on Jun. 10, 2014, https://www.youtube.com/watch?v=B43vT_1GnR0, 33 pages of screenshots.

"Affordable Clear Braces—Smile Care Club" video, uploaded to YouTube on Mar. 30, 2015, https://www.youtube.com/watch?v=Qk-VhbH1RVM, 97 pages of screenshots.

"Clear Braces . . . At Home??! Review—Before & After—Cost" video, uploaded to YouTube on Oct. 7, 2014, https://www.youtube.com/watch?v=9wrwhRTPjtk&t, 132 pages of screenshots.

"Invisalign Manufacturing Process English" video, uploaded to YouTube on Apr. 7, 2014, https://www.youtube.com/watch?v=vsR0_wTR2a8, 125 pages of screenshots.

(56) References Cited

OTHER PUBLICATIONS

"Smile Care Club Unboxing, Review, Tutorial" video, uploaded to YouTube on May 1, 2015, https://www.youtube.com/watch?v=p7Y5fMRnJWE, 126 pages of screenshots.
"Speak Out Game—Ellen Show with Khloe Kardashian and Kevin Hart", uploaded to YouTube on Oct. 11, 2016, https://www.youtube.com/watch?v=RDILAiBFRLY, 50 pages of screenshots.
"Step 1! Working on my Smile . . . Smile Care Club" video, uploaded to YouTube on Jan. 4, 2015, https://www.youtube.com/watch?v=T_F3Xt4Og7w, 87 pages of screenshots.
Do It Yourself Dental Impression Kit, Apr. 30, 2016, 2 pages.
ITero Element Orthodontic Patient Video, Uploaded to YouTube Apr. 4, 2016, https://www.youtube.com/watch?v=Ca69CuWqHCw, 33 pages of screenshots.
Smile Care Club Review, URL: https://www.youtube.com/watch?v=jpAjhJqi6vc, Mar. 26, 2016, 260 pages of screenshots.
Smile Care Club, "Impression Kit", Jul. 21, 2014, available for retrieval at URL https://vimeo.com/wmvproductions/review/115725718/28854a7f49, 43 pages of screenshots.
Smile Care Club, "Impressions—New Box", 2015,available for retrieval at URL https://vimeo.com/wmvproductions/review/137176701/d45be82d56, 24 pages of screenshots.
Smile Care Club, "Impressions—Old Box", 2015,available for retrieval at URL https://vimeo.com/wmvproductions/review/137176599/0b8020929d, 21 pages of screenshots.
Smile Care Club, "Impressions ReEdit", 2016,available for retrieval at URL https://vimeo.com/wmvproductions/review/168249998/0b75310374, 32 pages of screenshots.
Smile Care Club, "Impressions", 2015,available for retrieval at URL https://vimeo.com/wmvproductions/review/136533463/1a8515abf5, 10 pages of screenshots.
Smile Care Club, "Promo", 2014, available for retrieval at URL https://vimeo.com/wmvproductions/review/115725719/9c8235cdf2, 25 pages of screenshots.
SmileCareClub promo video uploaded on Jun. 6, 2014 https://www.youtube.com/watch?v=h7x8BwWXUsk, 33 pages of screenshots.
Summerfelt, Fred F., "Teledentisty-Assisted, Affiliated Practice for Dental Hygienists: An Innovative Oral Health Workforce Model", Journal of Dental Education, vol. 75, No. 6, Jun. 2011, pp. 733-742.
"Startup Story and Hiring Help from Smile Direct Club Founder Doug Hudson" on relode.com, published Aug. 11, 2015, available at https://www.relode.com/blog/startup-story-and-hiring-help-from-smilecareclub-founder-doug-hudson, 2 pages.
Albert et al., "Smile Care Club Review—My experience straightening my teeth with smile care", https://smilecareclubreview.wordpress.com/page/1/, relevant web posts published from Jan. 9, 2015-Mar. 4, 2015, accessed online Dec. 30, 2019 (Year: 2015), 8 pages.
Grindguard, "How to use your dental impression kit", http://www.grindguardpm.com/support/how-to-use-your-dental-impression-kit/ Feb. 9, 2017, accessed online Jan. 3, 2020 (Year: 2017), 5 pages.
Hoabie et al., "Evaluation Kit in Mail", https://smilecareclub.wordpress.com/ Mar. 27, 2015, accessed online Jan. 2, 2020 (Year: 2015), 3 pages.
International Search Report and Written Opinion for International Application No. PCT/US2019/054958, dated Dec. 17, 2019, 8 pages.
ITero Element Orthodontic Patient Video, Uploaded to YouTube Apr. 4, 2016, https://www.youtube.com/watch?v=Ca69CuWqHCw.
Mouthpiece Guy et al.: "Mouthpiece Guy vs. The Competition: Impression Kits", www.youtube.com/watch?v=tYOjMtYWQOQ&feature=youtu.be, Feb. 23, 2018, 20 pages of screenshots.
Buschang et al., "Comparative Time Efficiency of Aligner Therapy and ConventionaL Edgewise Braces", Angle Orthodontist, vol. 84, No. 3, 2014, 6 pages.
Complaint for Patent Infringement, *SmileDirectClub, LLC* v. *Candid Care Co.*, Case No. Case 1:20-cv-00583-UNA, Apr. 29, 2020, 45 pages.
Defendant Candid Care Co's Opening Brief in Support of its Motion to Dismiss, *SmileDirectClub, LLC* v. *Candid Care Co.*, Case No. Case 1:20-cv-00583-CFC, Jun. 19, 2020, 147 pages.
Defendant Candid Care Co's Reply Brief in Support of its Motion to Dismiss, *SmileDirectClub, LLC* v. *Candid Care Co.*, Jul. 31, 2020, 17 pages.
SmileDirectClub, LLC's Opposition to Candid Care Co.'s Motion to Dismiss, *SmileDirectClub, LLC* v. *Candid Care Co.*, Case No. Case 1:20-cv-00583-CFC, Jul. 17, 2020, 29 pages.
Memorandum Opinion, *SmileDirectClub, LLC* v. *Candid Care Co.*, Case 1:20-cv-00583-CFC, Dec. 7, 2020, 25 pages.
Notice of Appeal, *SmileDirectClub, LLC* v. *Candid Care Co.*, Case 1:20-cv-00583-CFC, Dec. 8, 2020, 2 pages.
From Home Dental, Web page: https://web.archive.org/web/20161021220200/https://fromhomedental.com, Oct. 21, 2016, 4 Pages.
"Why I am Straightening My Teeth With SmileDirectClub", Gluesticks Blog, https://gluesticksblog.com/smiledirectclub-review/, Aug. 26, 2015, 19 pages.
Beers et al., "Computer-assisted treatment planning and analysis", Orthod Caniofacial Res 6(Suppl. 1), 2003; 117-125.
Bhambal et al., "Teledentistry: potentials unexplored!", J. Int Oral Health, Oct. 2010, vol. 2 (Issue 3).
Cooper et al.,"Knowledge, attitudes, and confidence levels of dental hygiene students regarding teledentistry: A pilot study." The Internet Journal of Allied Health Sciences and Practice. Oct. 2007, vol. 5 No. 4.
Ercoli et al., "A comparative study of two different clear aligner systems", Progress in Orthodontics, 2014.
Fabels et al., "Interexaminer and intraexaminer reliabilites of 3-dimensional orthodontic digital setups", American Journal of Orthodontics and Dentofacial Orthopedics, Dec. 2014, vol. 146, Issue 6.
Forever Aligned Club, "Straight Teeth Forever", https://www.foreveralignedclub.com/straight-teeth-forever/, May 26, 2017, 3 pages.
Garino et al., "The iTero Intraoral Scanner in Invisalign Treatment: A Two-year Report", JCO, Feb. 2014.
Groth et al., "Three-Dimensional Printing Technology", JCO, 2014.
Hayashi et al., "Assessment of the accuracy and reliability of new 3-dimensional scanning devices", American Journal of Orthodontics and Dentofacial Orthopedics, Oct. 2013, vol. 144, Issue 4.
Jain et al., "Teledentistry: Upcoming Trend in Dentistry", J Adv Med Dent Scie 2013; 1(2): 112-115.
James Hunt; SmileDirectClub impression kit, https://www.youtube.com/watch?v=3u2KI9Mphey, uploaded Jan. 16, 2017, 19 pages of screenshots.
Jampani et al., "Applications of teledentistry: A literature review and update", Journal of Int Society of Preventive & Community Dentistry, Jul.-Dec. 2011; 1(2): 37-44.
Jones, Perry "The iTero optical scanner for use with Invisalign: A descriptive review", ineedce.com, Feb. 2012.
Kravitz et al., "Intraoral Digital Scanners", JCO, 2014, vol. 48, No. 6.
Kuncio, Daniel A. "Invisalign: Current guidelines for Effective Treatment", NY State Dental Journal, Mar. 2014.
Lau et al., "Computerised Imaging, Virtual Treatment Planning and Orthodontic Treatment of Dental Malocclusions Using the Invisalign Appliance", The Hong Kong Medical Diary, vol. 9, No. 10, Oct. 2004.
Lin et al., "3D CAD for Design of Invisible Tooth Aligner", Proceedings of the 2005 IEEE Int Conf on Mechanics, Jul. 10-12, Taipei, Taiwan.
Martin et al., "Orthodonticscanners: what's available?", Journal of Orthodontics, vol. 000, 2014, 000-000.
Martorelli et al., "A comparison between customized clear and removable orthodontic appliances manufactured using RP and CNC techniques", Elsevier, Dental Materials 29 (2013).
Monika et al., "Teledentistry: An Overview." J Adv Med Dent Scie Res 2015;3(2):88-91.
Relode, "Startup Story and Hiring Help from SmileDirect Club Founder Doug Hudson"; https://www.relode.com/blog/startup-story-and-hiring-help-from-smiledirectclub-founder-doug-hudson, Aug. 11, 2015, 3 pages.

(56) References Cited

OTHER PUBLICATIONS

Shailee et al., "Teledentistry the future of dental practice", Indian J Dent Adv 2013; 5(2): 1195-1199.

SmileDirectClub; Frequent Questions htttps://web.archive.org/web/20170409175711/https://smiledirectclub.com/faq/ Apr. 9, 2017, 7 pages.

SnapCorrect, "What Does My Impression Evaluation Kit Include", https://support.snapcorrect.com/support/solutions/articles/32000019500-what-does-my-impression-evaluation-kit-include, Sep. 18, 2017 1 page.

SnapCorrect, "What Does the 'Return by' Sticker Date Mean", https://support.snapcorrect.com/support/solutions/articles/32000022084-what-does-the-return-by-sticker-date-mean, Feb. 5, 2018 1 page.

SnapCorrect, Snap Correct Impressions, https://www.youtube.com/watch?v=yywqIDSabew, uploaded Oct. 6, 2017, 6 pages of screenshots.

SnapCorrect, SnapCorrect Truly Invisible Aligners, https://youtube.com/watch?v=yywqIDSabew, uploaded Jul. 27, 2017, 8 pages of screenshots.

Summerfelt, Fred F."Teledentistry-Assisted, Affiliated Practice for Dental Hygienists: An Innovative Oral Health Workforce Model", Journal of Dental Education, 2011.

Szuhanek et al., "Application of Thermoplastic Materials in the Fabrication of Orthodontic Aligners", Materiale Plastice, 52, No. 3, 2015.

Szuhanek et al., "The Role of Digital Setup in the Orthodontic Treatment with Plastic Aligners", Materiale Plastice, 52, No. 4, 2015.

Taneva et al., "3D Scanning, Imaging, and Printing in Orthodontics", IntechOpen, 2015.

Thukral et al., "Invisalign: Invisible Orthodontic Treatment—A Review." J Adv Med Dent Scie Res 2015;3(5):S42-S44.

Federal Circuit Affirmance on the '522 patent Case No. 2021-1446 dated Aug. 17, 2021.

\* cited by examiner

FIG. 4

```
NAME ON CREDIT CARD

BILLING ADDRESS

CITY

STATE                ZIP CODE

CREDIT CARD NUMBER

MM/YYYY              SECURITY CODE

E-MAIL ADDRESS
```

402

Due to high demand, we ask that you provide your credit card information to hold your reservation. A refundable $25 hold will be placed on your credit card for holding your reservation. This hold will not be billed to you unless you do not show up for your appointment.

HOLD MY RESERVATION

OPT OUT

404    406

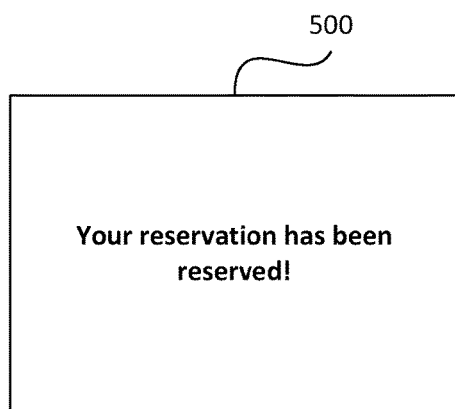

Your reservation has been reserved!

FIG. 5A

We will still hold your reservation!

Even though you didn't provide your credit card information, we will still hold your reservation – just for you!

FIG. 5B

Health and Consent Questionnaire

| | |
|---|---|
| Yes No | Do you have a bonded retainer? |
| Yes No | Do you have crowns? |
| Yes No | Do you have any bridgework? |
| Yes No | Do you have an impacted tooth? |
| Yes No | Do you have veneers? |
| Yes No | Do you feel any pain in any of your teeth? |
| Yes No | Do you authorize us to administer an intraoral scan? |

SYSTEMS AND METHODS FOR MOBILE DENTITION SCANNING

CROSS-REFERENCE TO RELATED APPLICATIONS

This application is a continuation-in-part of U.S. patent application Ser. No. 16/130,762, filed Sep. 13, 2018, which claims the benefit of and priority to U.S. Provisional Patent Application No. 62/660,141, filed Apr. 19, 2018. U.S. patent application Ser. No. 16/130,762 is also a continuation-in-part of U.S. patent application Ser. No. 15/725,430, filed Oct. 5, 2017, which claims the benefit of and priority to U.S. Provisional Patent Application No. 62/522,847, filed Jun. 21, 2017. All of the aforementioned applications are incorporated herein by reference in their entirety.

TECHNICAL FIELD

The present disclosure relates generally to the field of intraoral scanning, and more specifically, to intraoral scanning for generating a three-dimensional image of a user's teeth that is used in treating misalignment of the user's teeth.

BACKGROUND

A dental impression can be used to make a digital model of a user's teeth. Alternatively, a three-dimensional ("3D") scanner can be used to create a digital model of a user's teeth. For example, a user may visit a location at which a location employee uses an intraoral scanner to scan the user's teeth, with the scan being used to create a digital model of the user's teeth. In order for an intraoral scan of the user's teeth to be taken, the user may need to determine where a location that offers intraoral scanning is and how to travel to the location. If the closest location is far away from the user, it may be inconvenient or prohibitive for the user to travel to that location. Additionally, in some cases, the user may be unaware that a location that offers intraoral scanning exists such that the user can have an intraoral scan of the user's teeth taken.

SUMMARY

One embodiment relates to a mobile intraoral scanning site. The mobile intraoral scanning site includes a vehicle and one or more three-dimensional intraoral scanners provided on the vehicle and configured to perform intraoral dentition scans of users on the vehicle. The vehicle may include at least two compartments configured to be used as scan stations for performing the intraoral dentition scans of users on the vehicle. The vehicle may further include a reception compartment separating the two scan station compartments. The vehicle may further include a reception compartment separating the two scan station compartments. At least one of the scan station compartments may further include a fixed chair configured to be used by a user during an intraoral dentition scan. At least one compartment may further include a disability access entrance. The vehicle may be retrofitted to be used for the mobile intraoral scanning site. The one or more three-dimensional intraoral scanners may be wall-mounted on the vehicle. The vehicle may be with an intraoral connection such that the intraoral dentition scans are uploaded to a cloud server via the internet connection.

Another embodiment relates to a method for intraoral dentition scanning. The method includes providing a mobile intraoral scanning site including a vehicle and one or more three-dimensional intraoral scanners provided on the vehicle and performing, by the one or more three-dimensional intraoral scanners, one or more intraoral dentition scans on one or more users on the vehicle. The vehicle may include at least two compartments configured to be used as scan stations for performing the one or more intraoral dentition scans on the vehicle. The vehicle may further include at least two compartments configured to be used as scan stations for performing the one or more intraoral dentition scans on the vehicle. The vehicle may further include a reception compartment separating the two scan station compartments. At least one of the scan station compartments may further include a fixed chair configured to be used by a user during an intraoral dentition scan. At least one compartment may include a disability access entrance. The vehicle may be retrofitted to be used for the mobile intraoral scanning site. The one or more three-dimensional may be wall-mounted on the vehicle.

Another embodiment relates to a method for intraoral dentition scanning. The method includes providing a mobile intraoral scanning site including a vehicle and one or more three-dimensional intraoral scanners provided on the vehicle, locating the vehicle at a site for a limited period of time, and sending messages associated with the mobile intraoral scanning site to a plurality of individuals, the messages inviting the plurality of individuals to schedule an appointment to receive an intraoral dentition scan at the vehicle. The method includes performing, by the one or more three-dimensional intraoral scanners, one or more intraoral dentition scans on one or more users on the vehicle. The vehicle may include at least two compartments configured to be used as scan stations for performing the one or more intraoral dentition scans on the vehicle.

Various other embodiments and aspects of the disclosure will become apparent based on the drawings and detailed description of the following disclosure.

BRIEF DESCRIPTION OF THE DRAWINGS

FIG. 4 shows a reservation hold screen associated with the appointment management system of FIG. 1 according to an exemplary embodiment.

FIG. 5A and FIG. 5B show example confirmation windows associated with the appointment management system of FIG. 1 according to an exemplary embodiment.

FIG. 7 shows a health and consent information screen displayed on a user device for enabling the user to provide health and consent information according to an exemplary embodiment.

DETAILED DESCRIPTION

The present disclosure is directed to systems and methods for conducting an intraoral scan of a user at a location. A user can request an appointment at an intraoral scanning site. For example, the user can request an appointment in advance of the requested appointment time (e.g., online, via a mobile application, via a telephone call) or the user can request an appointment at the time of requested appointment (e.g., a "walk in"). In requesting the appointment at the intraoral scanning site, the user can provide various information for reserving the appointment, such as a reason for making the appointment (e.g., misaligned teeth) or a dental condition of the patient (e.g., having crowns, an impacted tooth). The user can make the request online (e.g., via an internet scheduling website associated with the intraoral scanning site). When the appointment timeslot is held for the user, one or more scheduling alerts can be communicated to the user (e.g., confirmation notification, reminder notification, appointment modification query). Upon arriving at the appointment, the user can provide health history and consent information. The user can receive the intraoral scan, and upon confirmation from the user to purchase the aligners, one or more sets of aligners configured to modify the alignment of the user's teeth can be sent to the user.

The systems and methods described herein may have many benefits including, but not limited to, increasing user excitement about the alignment process, increasing the likelihood of a user showing up for their appointment, and increasing the likelihood of a user purchasing aligners at the intraoral scanning site, as will be discussed in greater detail below.

Figure 1:
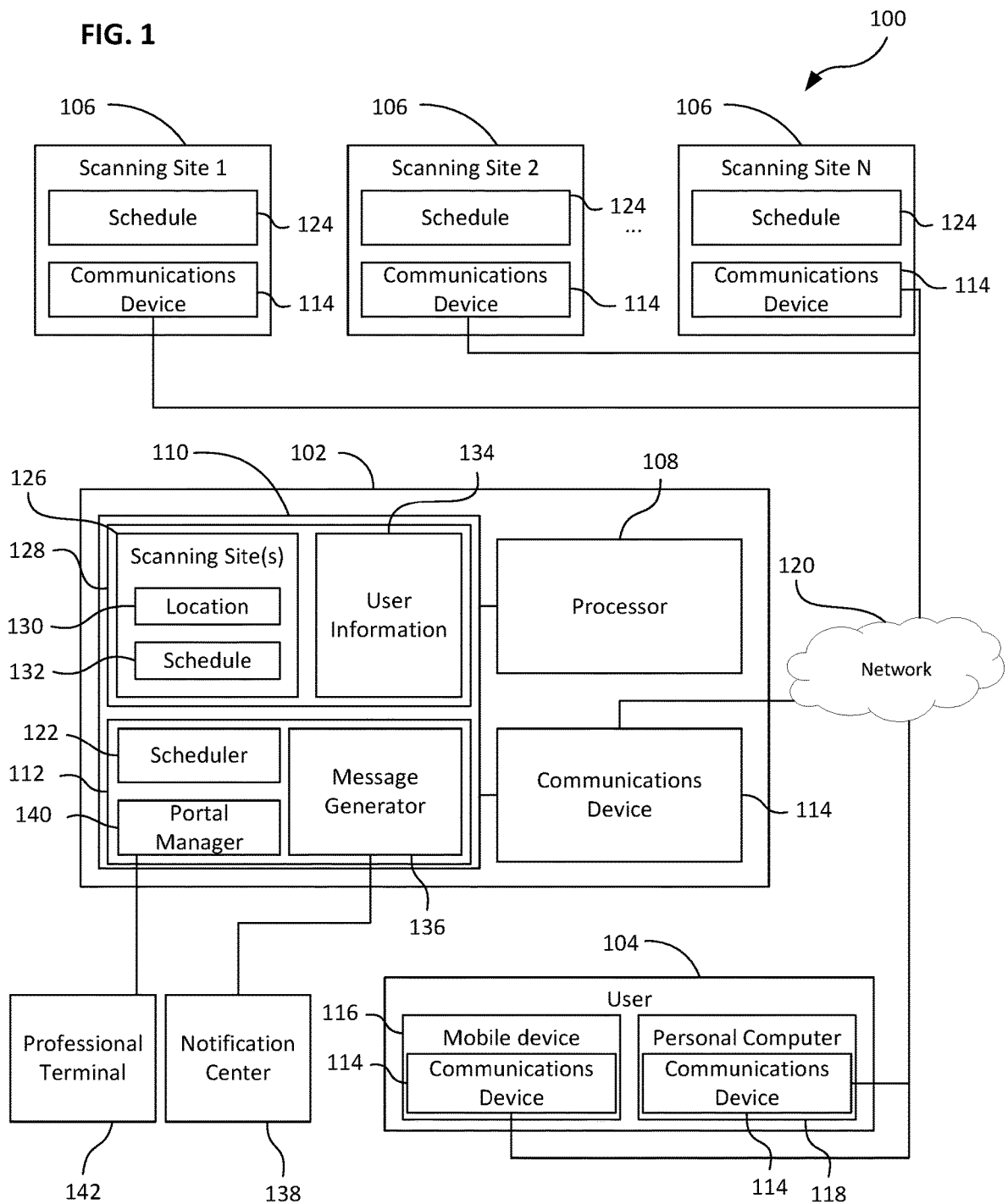
FIG. 1 shows an appointment management system according to an exemplary embodiment.

Referring to FIG. 1, an appointment management system 100 is shown. The appointment management system 100 includes a computing system 102, a mobile device 116 of a user 104, a personal computer 118 of the user 104, and a plurality of intraoral scanning sites 106.

The computing system 102 includes a processor 108 and memory 110. Processor 108 may be a general purpose or specific purpose processor, an application specific integrated circuit (ASIC), one or more field programmable gate arrays (FPGAs), a group of processing components, or other suitable processing components. Processor 108 may be configured to execute computer code or instructions stored in memory 110 or received from other computer readable media (e.g., CDROM, network storage, a remote server, etc.) to perform one or more of the processes described herein. Memory 110 may include one or more data storage devices (e.g., memory units, memory devices, computer-readable storage media, etc.) configured to store data, computer code, executable instructions, or other forms of computer-readable information. Memory 110 may include random access memory (RAM), read-only memory (ROM), hard drive storage, temporary storage, non-volatile memory, flash memory, optical memory, or any other suitable memory for storing software objects and/or computer instructions. Memory 110 may include database components, object code components, script components, or any other type of information structure for supporting the various activities and information structures described in the present disclosure. Memory 110 may be communicably connected to processor 108 via a processing circuit and may include computer code for executing (e.g., by processor 108, etc.) one or more of the processes described herein.

The memory 110 is described below as including various circuits 112. While the exemplary embodiment shown in the figures shows each of the circuits 112 as being separate from one another, it should be understood that, in various other embodiments, the memory 110 may include more, less, or altogether different circuits 112. For example, the structures and functions of one circuit 112 may be performed by another circuit 112, or the activities of two circuits 112 may be combined such that they are performed by only a signal circuit 112. Additionally, it should be understood that any of the functionalities described as being performed by a circuit 112 that is a part of the controller 112 may also be performed by a separate hardware component having its own processors, network interfaces, etc.

As shown in FIG. 1, the appointment management system 100 includes one or more communications device(s) 114. The communications device(s) 114 can be or include components configured to transmit and/or receive data from one or more remote sources. For instance, each of the intraoral scanning site(s) 106 may include a respective communications device 114, the user 104 may have one or more communications device(s) 114 embodied on the user's 104 mobile device 116, personal computer 118, etc., and/or the computing system 102 may include a communications device 114. Each of the respective communications devices 114 may permit or otherwise enable data to be exchanged between the user 104, the intraoral scanning site(s) 106, and/or the computing system 102. The communications device 114 may communicate via a network 120. The network 120 may be a Local Area Network (LAN), a Wide Area Network (WAN), a Wireless Local Area Network (WLAN), an Internet Area Network (IAN) or cloud-based network, etc. In some implementations, the communications device(s) 114 may access the network 120 to exchange data with various other communications device(s) 114 via cellular access, a modem, broadband, Wi-Fi, satellite access, etc.

Generating an Appointment

In some implementations, the user 104 may access a website (or other network-based portal) associated with the appointment management system 100. The user 104 may book an appointment at an intraoral scanning site 106 on the website. The user 104 may be directed to the website through, for instance, an advertisement on the user's 104 social media account. Additionally or alternatively, the user 104 may search for (e.g., on the internet, etc.) the website associated with the appointment management system 100.

Additionally or alternatively, the user 104 may receive a message directing them to the website to book an appointment at an intraoral scanning site 106. The processor 108 may control the communications device 114 to send the message to the user 104 in response to various conditions. For instance, the processor 108 may determine that the user 104 previously signed up to receive an in-home dental impression kit and never returned the completed kit. The processor 108 may identify a time between an order date (or shipment date) of the dental impression kit and the current date. The processor 108 may compare the identified time to a threshold time indicative of the user 104 likely not returning impressions from the dental impression kit. Where the identified time exceeds the threshold time, the processor 108 may automatically generate and send the message to the user 104. As another example, the processor 108 may determine that the impressions received from the user 104 were, for instance, incomplete. A technician may review the impressions (or a scan thereof) to determine their suitability for manufacturing dental aligners. When the impressions are determined to be incomplete, the technician may flag the impressions as incomplete. When the impressions are flagged, the processor 108 may automatically generate and send the message to the user 104 prompting the user to schedule an intraoral scan.

The website may include a home page, an instructional page detailing how the customer aligner process works, a results page, a locations page, and/or additional or alternative pages. Each of these pages may present different information to the user 104. For instance, the home page may present information pertaining to an overall user experience. The instructional page may present a step-by-step overview starting from an appointment to receiving customized aligners. Additionally, the instructional page may present a video to the user 104. The video may include graphics and/or text that show how the customized aligners reposition the user's 104 teeth, among other information. The video may also show the user 104 what to expect upon arrival at their appointment location, should they choose to book an appointment. The results page may include before-and-after pictures (or a rolling video of before-and-after pictures) of previous users who have used aligners to reposition their teeth. The locations page includes locations associated with each of the respective intraoral scanning sites 106.

Figure 2:
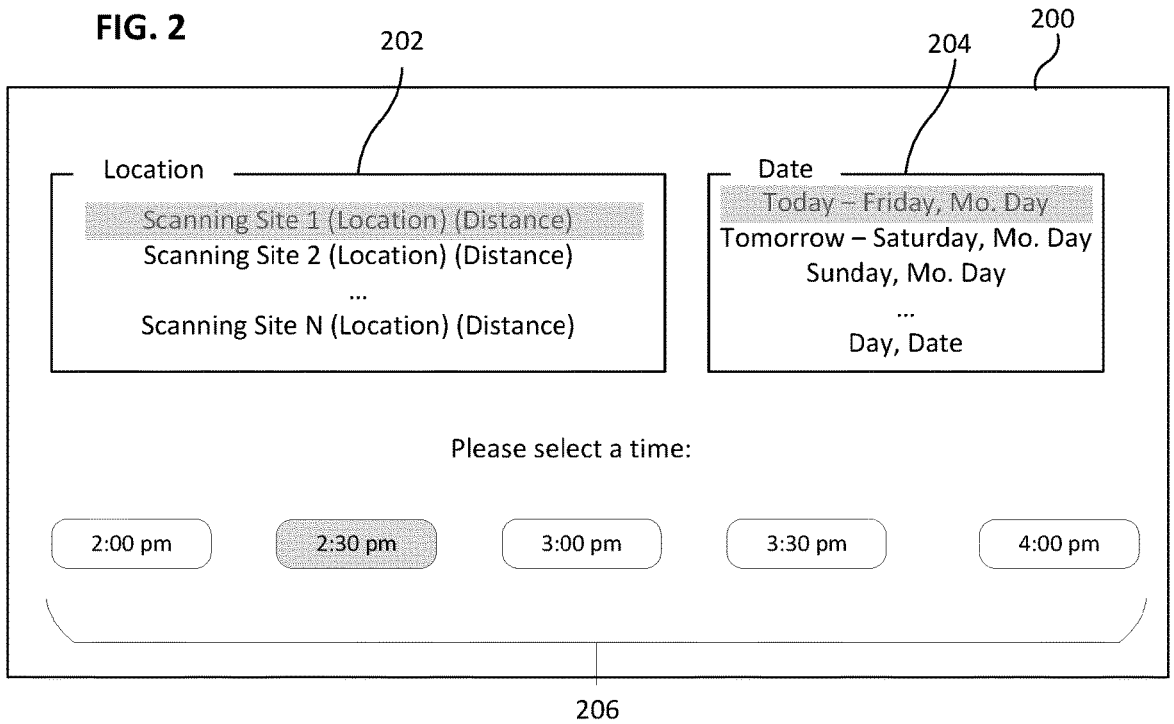
FIG. 2 shows a reservations screen associated with the appointment management system of FIG. 1 according to an exemplary embodiment.

Referring now to FIG. 1 and FIG. 2, the user 104 may access the locations page of the website. Specifically shown in FIG. 2 is a reservation page 200 which may be a portion of the locations page or a portion of the home page.

In some embodiments, the computing system 102 may include a scheduler 122. The scheduler can be or include instructions that, when executed by the processor 108, cause the processor 108 to generate and/or manipulate pages and displays for scheduling an appointment at an intraoral scanning site 106. While shown as embodied on memory 110 of the computing system 102 102, in some implementations, the scheduler 122 may be separate from the computing system 102. For instance, the scheduler 122 may be located remotely from the computing system 102. In instances such as these, the scheduler 122 may have a separate processor 108 and memory 110 (a dedicated processor and memory, for example). A user 104 may schedule an intraoral scan at a particular intraoral scanning site 106 via the website. The website may be controlled by the processor 108 using instructions from the scheduler 122. Following the intraoral scan, the user 104 may, in some instances, order aligners that are customized for the user 104. For instance, the user 104 may be satisfied with the overall process at the intraoral scanning site 106 and results of other users 104. Therefore, the user 104 may purchase aligners for aligning the user's 104 teeth. The aligners may be constructed of a polymer material, such as Polyethylenterephthalat-Glycol Copolyester (PET-G), which is thermoformed to positive molds (or models) of the user's 104 dentition at various intervals between a starting position and an ending position. The positive molds of the user's dentition 104 may be generated based on the treatment plan. The aligners may be used by the user 104 in stages to move the user's teeth towards the ending position. For example, the user 104 may be directed to wear a first aligner during a first month, a second aligner during a second month, a third aligner during a third month, and so on for a treatment period. These aligners may be shipped to the user 104 following production of the aligners (e.g., at a fabrication site which generates or otherwise produces the aligners). In some instances, the aligners may be shipped in stages, all at once in one box, etc. Each of the aligners may be administered by the user in a predetermined sequence and for a predetermined duration. For instance, a first aligner (which corresponds to a starting position of the user's teeth) may be administered by the user for a duration (e.g., a month, 90 days, etc.), a second (and additional intermediate) aligner(s) may be administered by the user for the same duration, and a final aligner may be administered for the same duration. Each of these aligners may move the user's teeth from the starting position to one or more intermediate positions, and from the one or more intermediate positions to the final positions based on the treatment plan.

As shown in FIG. 2, the reservation page 200 includes locations 202, dates 204, and times 206. Included in the locations 202 is information corresponding to each of the intraoral scanning site(s) 106. While each of the intraoral scanning site(s) 106 are shown as included, in some embodiments, only a subset of intraoral scanning site(s) 106 may be shown. For instance, the intraoral scanning site(s) 106 which are located nearest to the user 104 may be shown. As one example, the processor 108 may receive data from a communications device 114 associated with the user 104 (e.g., the mobile device 116, personal computer 118, etc.). The data may include location-based data associated with the user 104. The processor 108 may use this data to select, from each of the intraoral scanning site(s) 106, a subset of intraoral scanning site(s) 106 to include in the locations 202. As another example, the user 104 may be prompted to provide a zip code. The processor 108 may use the zip code provided by the user 104 to determine intraoral scanning site(s) 106 that are located nearest to (or within) the zip code.

In some implementations, a user 104 may search for specific locations 202 (instead of selecting ones that are nearest to the user's 104 location). The user 104, for instance, may be traveling to a different city than their city of residence and may want to schedule an appointment at an intraoral scanning site 106 located in that different city. As a result, the user 104 is not limited to scheduling appointments at intraoral scanning sites 106 in their own city, but may schedule appointments at any of the intraoral scanning sites 106. In implementations such as these, the user 104 may provide a zip code that is different from their current zip code (e.g., the zip code associated with the city to which they are traveling).

In still other implementations, one or more of the intraoral scanning sites 106 may be a mobile intraoral scanning site 106. For instance, the mobile intraoral scanning site 106 may be implemented in a vehicle (e.g., an automobile, a truck, a van, a bus, etc.), as part of a kiosk (e.g., located within another store or within a shopping mall), or comprise a pop-up location in operation for only a limited time period (e.g., one day, one week, one month). The mobile intraoral scanning site 106 may be included in the locations 202 on the reservation page 200. As will be described in further detail below, a user 104 may be able to arrange for the mobile intraoral scanning site 106 to travel to a set location (e.g., a location set by the user, such as their home or place of business), and the user 104 may receive an intraoral scan at the set location.

Upon selecting a location 202 of an intraoral scanning site 106 from the list of locations 202 of intraoral scanning sites 106, the user 104 may select an available date from the list of dates 204. Each intraoral scanning site 106 may maintain a schedule 124. The schedule 124 may be maintained locally (e.g., at each respective intraoral scanning site 106, etc.) and communicated to the computing system 102. The scheduler 122 can include instructions to access the schedule 124 of the intraoral scanning site 106 selected by the user 104 and determine available days/times for an appointment for the user 105 based on the schedule 124 for the intraoral scanning site 106. The scheduler 122 can include instructions to display available times and dates for the intraoral scanning site 106 based on the schedule 124 associated with the intraoral scanning site 106. Additionally or alternatively, the schedule 124 may be a cloud-based schedule that is remotely accessible by the processor 108 and by the respective intraoral scanning site 106. In implementations such as these, the memory 110 may store intraoral scanning site data 126 corresponding to each respective intraoral scanning site 106. The intraoral scanning site data 126 may be stored in a database 128 within memory 110. The intraoral scanning site data 126 may include a location 130 associated with the intraoral scanning site 106 (or other information usable to identify a particular intraoral scanning site 106) and a corresponding schedule 132 for the intraoral scanning site 106. The scheduler 122 can include instructions to determine the schedule for the selected location 202 of the intraoral scanning site 106 by cross-referencing data for the selected location 202 with location 130 within the intraoral scanning site data 126. Following cross-referencing the data for the selected location 202, the scheduler 122 can include instructions to identify the schedule for the corresponding selected location 202.

In each of these arrangements, the scheduler 122 can include instructions to identify available appointment times for the intraoral scanning site 106. These available appointment times may be presented to the user 104 for selection and booking an appointment.

As shown in FIG. 2, the intraoral scanning site(s) 106 may have extended hours (e.g., open nights, weekends, etc.). In implementations such as these, the user 104 may be more likely to schedule an appointment when the hours are extended due to a lessened likelihood of a scheduling conflict between the user 104 and a given intraoral scanning site 106.

The processor 108 may access the schedule 124, 132 for the selected location 202 to determine available dates via the instructions from the scheduler 122. The processor 108 may display the available dates in the list of dates 204. Following a selection of an available date from the list of dates 204, the times available for the selected date may be displayed to the user 104. The processor 108 may determine the available times in the same manner in which the available dates are determined. The user may select an available time to book their scan from the list of available times 206.

While described herein as the user first selecting a location, in some embodiments, the user may first select a preferred date and/or time and available locations (and/or dates and locations) may then be displayed based on the selected preferred date and/or time (and/or dates and locations). In each of these implementations, the user 104 may reserve a time at a particular intraoral scanning site 106, and at the reserved time, the user 104 may arrive at the particular intraoral scanning site 106 and receive their intraoral scan, as will be discussed in further detail below.

In some implementations, the user 104 may select the mobile intraoral scanning site 106. In implementations such as these, the processor 108 may identify a schedule 124, 132 associated with the mobile intraoral scanning site 106 using instructions from the scheduler 122. The user 104 may request a date 204 and time 206 that is available for the mobile intraoral scanning site 106. The user 104 may then provide a location to arrange the appointment with the mobile intraoral scanning site 106. The mobile intraoral scanning site 106 may have a predetermined radius (e.g., 10 miles, 20 miles, 25 miles, 50 miles, etc.) within which the mobile intraoral scanning site 106 operates. The user 104 may provide a location within the predetermined radius. At the reserved time, the mobile intraoral scanning site 106 may be driven to the location provided by the user 104. The user 104 may similarly arrive at the provided location at the reserved time and receive an intraoral scan, as will be discussed in further detail below.

Figure 3:
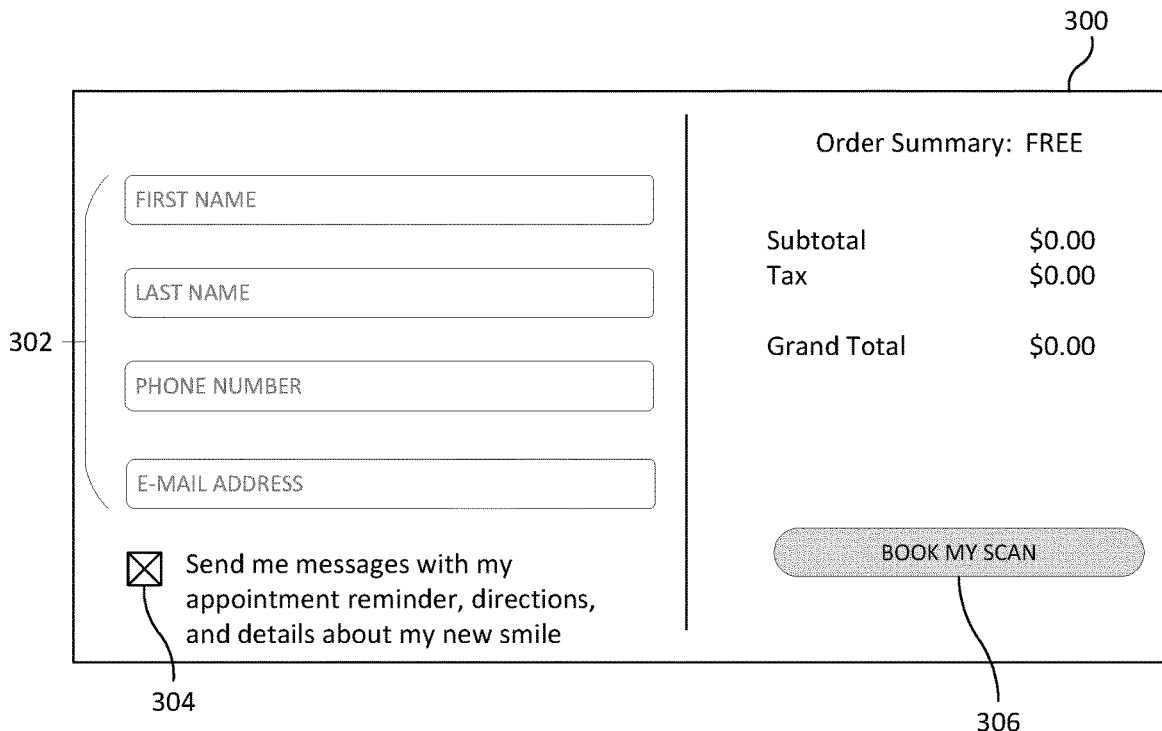
FIG. 3 shows a booking screen associated with the appointment management system of FIG. 1 according to an exemplary embodiment.

Referring now to FIG. 3, following the user 104 selecting an available time 206 (e.g., as shown in FIG. 2), the scheduler 122 can include instructions to direct the user 104 to a booking screen 300. At the booking screen 300, the user 104 may be prompted to provide various personal information 302 (e.g., first and last name, a phone number, an e-mail address, etc.). Additionally, the user 104 may be prompted to opt into (or not opt into) a messaging service by selecting box 304. The messaging service may provide one or more messages to the user 104 concerning the user's 104 booked appointment, as will be discussed in further detail below. The personal information 302 and data corresponding to whether the user 104 opted into the messaging service may be stored in database 128 in a user file 134. The user file 134 may be a file associated with the user 104 and may include various types of data associated with the user 104. The user file 134 nay be subsequently used for generating messages to the user 104 before and/or after the user's 104 appointment. The user file 134 may also include the intraoral scan, the treatment plan, progress information, photographs, etc.

As shown in FIG. 3, the appointment may be free to the user 104. In some implementations, the appointment may have a flat fee (e.g., $25, $95, etc.). In still other implementations, the appointment may have a booking hold which is not charged to the user 104. Following the user 104 providing their personal information, the user 104 may be prompted to book their scan by selecting button 306.

Referring now to FIG. 4, when the user 104 books their scan by selecting button 306 (of FIG. 3), the scheduler 122 can include instruction to direct the user 104 to a holding page 400. At the holding page 400, the user 104 may be prompted to provide credit card information 402. The credit card information 402 may be requested to hold the available time selected by the user 104 (e.g., as selected on reservation page 200). The credit card information 402 may be used to place a hold (for instance, $25) on the user's 104 credit card. In some implementations, the hold may be a refundable hold (e.g., the credit card for the user 104 is not billed or is refunded unless the user 104 does not show up for their appointment at the selected time).

In some implementations, the hold may be optional. For instance, the user 104 may be able to hold the reservation (through selection of button 404) or opt out of holding the reservation (through selection of button 406). The user 104 may provide their credit card information 402 and select button 404. In selecting prompt 404, confirmation window 500 may be displayed to the user 104 (e.g., indicating that the user's 104 reservation has been confirmed). Additionally, the user 104 may not provide their credit card information 402, and instead, opt out by selecting button 406. In some implementations, selecting button 406 may direct the user 104 back to the reservation page 200. In other implementations, selecting button 406 may cause confirmation window 502 to be displayed to the user 104 (e.g., indicating that the user's 104 reservation is still confirmed despite the user 104 not providing credit card information 402). By providing credit card information 402, the user 104 may be more likely to show up for their appointment, despite their credit card never being charged.

In one or more embodiments, following the user 104 reserving (and optionally holding) their appointment, the user 104 may want to reschedule their appointment. To do so, the user 104 may call the intraoral scanning site 106 to reschedule their appointment. Additionally, the user 104 may go onto the website associated with the appointment management system 100, provide log-in information or other identifying information to look-up their appointment and access, for instance, a user portal (as will be discussed in greater detail below). The user portal may include various appointment-related information including the time, date, and location for their appointment. Following the user's appointment, the user portal may include various treatment plan information (such as a virtual representation of the user's 104 treatment plan at different stages or a simulated representation of the user's 104 teeth through progression of the treatment plan), progress information provided by the user 104, etc., as will be discussed in greater detail below. The user 104 may select their appointment and reschedule their appointment in substantially the same manner by which the user 104 booked their appointment Pre-Appointment Messaging SERVICES Referring back to FIG. 1, when the user 104 opts into the messaging service (through selection of box 304 of FIG. 3), one or more messages may be automatically generated and communicated to the user 104 (e.g., via respective communications device(s) 114). For instance, the computing system 102 may include a message generator 136. The message generator 136 can be or include instructions that, when executed by processor 108, cause the processor 108 to generate a message to communicate to the user 104. The message generator 136 can include instructions to transmit the generated message to the user 104 via, for instance, the communications device 114 of the computing system 102 to the communications device 114 of the user's 104 mobile device 116 and/or personal computer 118. The message generator 136 can include instructions to identify a communications device 114 associated with the user 104 (e.g., by identifying the user file 134 associated with the user 104). The message generator 136 can include instructions to communicate the generated message to the user 104 upon one or more conditions, as will be discussed in further detail below. Accordingly, the various messages described herein may be communicated to the user's 104 mobile device 116 and/or the user's 104 personal computer 118. Various examples of messages will be discussed in turn below.

In some implementations, one or more messages that are generated via the message generator 136 may be communicated to a notification center 138. The notification center 138 may be, for instance, a call center. The messages that are communicated to the notification center 138 may be instructions to call a particular user 104 at a particular time to deliver a verbal message, as will be discussed in further detail below.

In some embodiments, the message generator 136 can include instructions for generating an appointment confirmation message. The message generator 136 can include instructions to determine when a user 104 has successfully reserved an appointment. The message generator 136 can include instructions to automatically communicate (e.g., via respective communications devices 114) the appointment confirmation message in response to the user 104 successfully reserving the appointment. The appointment confirmation message may be or include a message that indicates that the user's 104 appointment has successfully been reserved. In some implementations, the appointment confirmation message may include a link, which the user 104 may select, that causes the appointment to be automatically added to a calendar associated with the user 104. For instance, the appointment confirmation message may include a plurality of links associated with different types of calendar software. The user 104 may select the link corresponding to whichever type of calendar that is used by the user 104. Upon selecting the appropriate link, the appointment may automatically be added to the user's 104 calendar. The appointment added to the user's 104 calendar may include contact information associated with the corresponding intraoral scanning site 106, a location associated with the intraoral scanning site 106, time, and an expected duration of the appointment (e.g., 30 minutes).

In some embodiments, the message generator 136 can include instructions for generating one or more appointment reminder messages. The message generator 136 can include instructions to determine a current time and an appointment time (e.g., the time of the user's 104 appointment at the intraoral scanning site 106). The message generator 136 can include instructions to compare a time difference between the current time and appointment time to a threshold time. If the difference in time is less than (or equal to) the threshold time, the message generator can include instructions to automatically generate the appointment reminder message.

In some implementations, the threshold time may be set based on a number of days (e.g., two days, three days, a week, etc.) until the user's 104 appointment. In implementations such as these, the appointment reminder message may be a message reminding the user 104 that they have an upcoming appointment. The appointment reminder message may be generated when the user 104 books an appointment well in advanced. Accordingly, where the user 104 books an appointment for a number of days in advanced that is less than a threshold number of days (e.g., two days, three days, a week, etc.), the appointment reminder message may not be generated. As one non-limiting example, the user 104 may book an appointment on a Monday. Where the user 104 books the appointment for the next Friday, the user 104 may be reminded of their appointment through generation of an appointment reminder message on the upcoming Wednesday. However, where the user 104 books the appointment for the next day (e.g., Tuesday), the user 104 may not receive an appointment reminder message. The appointment reminder message that is communicated to the user 104 may include various information including, for instance, directions to the intraoral scanning site 106, a phone number for the intraoral scanning site 106, etc. Additionally, the appointment reminder message may include various information pertaining to the user's 104 appointment. For example, the appointment reminder message may include a health and consent questionnaire for the user 104 to fill out. In some implementations, the health and consent questionnaire may have a plurality of Yes/No questions corresponding to various health-related conditions. The responses to the questions may be defaulted to "No", whereby the user 104 may only need to change those answers to the questions that do apply to the user 104. Referring briefly to FIG. 7, the user 104 may be shown several questions which are defaulted to "No". The user 104, however, may have an impacted tooth and an indicator on the health and consent questionnaire for an impacted tooth is defaulted to "No". Accordingly, the user 104 may maintain all defaulted answers except for the question relating to impacted teeth, which the user 104 may switch to answer "Yes." Such arrangements may expedite the overall process for the user's 104 experience at the intraoral scanning site 106. As another example, the appointment reminder may include before-and-after pictures for previous customers (e.g., similar to those described above with reference to the results page). Such arrangements may increase excitement and anticipation of the appointment for the user 104.

In some implementations, the threshold time may be set based on a location of the user 104 (e.g., as determined based on data provided by the user's 104 mobile device 116 and/or personal computer 118) with respect to the location of the intraoral scanning site 106. In implementations such as these, the appointment reminder message may be a message reminding the user 104 to leave for their appointment. The threshold may be determined based on factors in addition to the location of the user 104 including, for instance, a distance between the respective locations, traffic between the respective locations, weather, time of day, day of the week, etc. The appointment reminder message that is communicated to the user 104 may include various information including, for instance, directions to the intraoral scanning site 106, a phone number for the intraoral scanning site 106, etc.

In some implementations, the message generator 136 may include instructions to generate multiple appointment reminder messages. For instance, the message generator 136 may generate a first appointment reminder message to remind the user 104 that they have an upcoming appointment and a second appointment reminder message to indicate to the user 104 that they should leave for their appointment (e.g., now, in 15 minutes, in one hour, etc.).

In some embodiments, the message generator 136 can include instructions to identify specific users 104 for voice messages. For instance, where the user 104 does not provide credit card information 402 (thus opting out of reserving the appointment), such information may be stored in the user file 134. Where the user 104 does not provide credit card information 402, the message generator 136 can include instructions to generate a prompt for a voice message to communicate to the notification center 138. The prompt may instruct a person at the notification center to initiate a telephone call with the user 104, in which the user 104 will be informed about the overall process and experience at the intraoral scanning site 106, and the user 104 may provide one or more concerns regarding their smile. The call may be initiated by the person at the notification center a certain number of days prior to the user's 104 appointment (e.g., three days, five days, etc.). The person may annotate (or record) the conversation, and portions thereof may be saved to the user file 134. In embodiments such as these, the voice message may increase user 104 excitement for the appointment and increase the likelihood that the user 104 shows up for their scheduled appointment.

Appointment Management at an Intraoral Scanning Site

Figure 6:
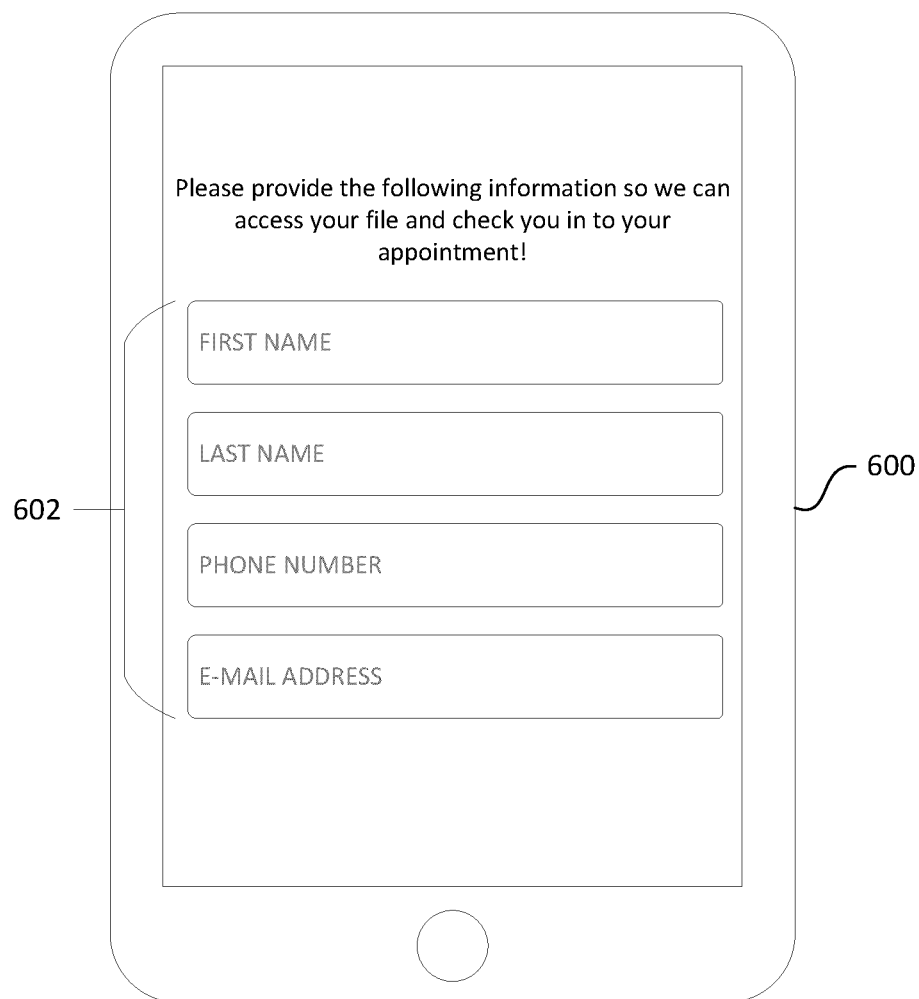
FIG. 6 shows a check-in screen displayed on a user device for enabling a user to check into an appointment according to an exemplary embodiment.

Referring now to FIG. 1 and FIG. 6, upon arrival at the intraoral scanning site 106, the user 104 may be presented with a user device 600. The user device 600 may be a tablet, for instance. The user 104 may be requested to provide personal information 602 (e.g., similar to the personal information 302) for accessing the user file 134. The processor 108 may retrieve the user file 134 associated with the user 104 and check the user 104 into their appointment. Where the user 104 does not show up within a predetermined timeframe (e.g., at the start time of their appointment, within five minutes after the start time, 10 minutes after their start time, etc.) the processor 108 may automatically indicate the user 104 did not show up for their scheduled appointment. The processor 108 may compare a time difference between the current time and the appointment start time to a predetermined timeframe. If the time difference exceeds the predetermined timeframe, the processor 108 may automatically indicate the user 104 did not show up for their scheduled appointment in the user file 134. Additionally or alternatively, a receptionist may indicate that the user 104 did not show up for their appointment in the user file 134. In some embodiments, the message generator 136 can include instructions for automatically generating a message to send to the user when the user is late for their appointment beyond a predetermined time frame (for instance, five minutes late). The message may ask the user to respond with whether they still plan on having an intraoral scan conducted, indicate that they do not need an appointment to receive their scan, prompt them to reschedule, etc.

In some instances, the intraoral scanning site 106 may include a screen (e.g., of a television or other display system) that displays before-and-after pictures of customers who previously used aligners. The before-and-after pictures may be similar to those described above with reference to the results page. The before-and-after pictures may be displayed on a rolling basis. In instances such as these, consumer confidence may be increased by observing historical results.

Referring now to FIG. 1 and FIG. 7, the user file 134 may include the health and consent questionnaire. Where the health and consent questionnaire was previously filled out by the user 104 (e.g., as it was received in an appointment reminder message), the health and consent questionnaire may be saved to the user file 134. However, where the health and consent questionnaire was not previously filled out by the user 104 (e.g., the user 104 never filled the questionnaire out or the questionnaire was never provided to the user 104), the user 104 may fill out the health and consent questionnaire via the user device 600. In some embodiments, where the user 104 switches an answer, a comment box is automatically generated and displayed to the user 104 prompting the user 104 to provide further details. For instance, where the user indicates that they are experiencing pain in their teeth, a comment box is automatically generated and displayed on the display of the user device 600. The user may provide an input, via the comment box, to elaborate on the pain in their teeth. While two examples of when the health and consent questionnaire are provided (e.g., following a reservation and following an appointment check-in but prior to the intraoral scan), the health and consent questionnaire may be provided to the user 104 to complete at any time throughout the scanning process after they arrive at the scanning location, such as during a break in procedures, following completion of the intraoral scan, etc. Accordingly, the present disclosure is not limited to any particular arrangement regarding when the health and consent questionnaire is completed by the user 104.

As shown in FIG. 7, the user device 600 may present the health and consent questionnaire to the user 104. As discussed above, the health and consent questionnaire may have a plurality of Yes/No questions corresponding to various health-related conditions. In some implementations, at least some of the questions for the health and consent questionnaire may be defaulted to a set response. For instance, the health-related questions for the questionnaire may be defaulted to "NO", whereas the consent-related questions for the questionnaire may be defaulted to "YES". In other instances, all of the questions may be defaulted to "NO". The user 104 can modify the responses to all the questions as needed. For instance, the user 104 may have bridgework and a question inquiring about whether the user 104 has bridgework is defaulted to "No". Accordingly, the user 104 may maintain the default answers to all the questions except for the question pertaining to bridgework. The user 104 may manually switch this answer to "Yes." In each of these implementations, the user's 104 experience at the intraoral scanning site 106 may be improved by expediting the health and consent questionnaire.

Following check-in and providing the responses to the health and consent questionnaire, the user 104 may be directed to a room where the user 104 will receive their intraoral scan. A technician at the scan shop 106 may administer the intraoral scan. The technician may administer the intraoral scan using, for instance, an iTero® scanner. As the technician administers the intraoral scan, the intraoral scanner may produce data which is visually represented on a display. The data may correspond to a three-dimensional scan of the user's 104 mouth. In some embodiments, the technician may administer the intraoral scan in a predetermined position. For instance, the technician may be instructed to administer the intraoral scan from over the user's 104 shoulder with the display in the field of view of the user 104. Accordingly, as the intraoral scanner generates data that is visually represented on the display, both the user 104 and technician may be able to observe the display. Such arrangements and instructions may enhance the user's 104 experience by engaging the user 104 in the scanning process.

In some embodiments, the administration of the intraoral scan may be recorded for quality assurance purposes. For instance, the room in which the user 104 has the intraoral scan administered may have a camera. The user 104 may approve or deny the recording. In some instances, the user 104 may be incentivized to approve the recording by, for instance, one free set of aligners or one free set of retainers.

In some embodiments, the user 104 may be shown a simulated movement of the user's teeth from the starting position (e.g., as represented by the three-dimensional scan) to a simulated final position. Such capabilities presently exist through use of the iTero® scanner.

Following administration of the intraoral scan, in some embodiments, a quality control technician may review and approve the intraoral scan. The quality control technician may be located at the intraoral scanning site 106. Additionally or alternatively, the quality control technician may be located remotely. The quality control technician may be a manager or other guide who has the authority to approve (or not approve) the intraoral scan. Where the quality control technician does not approve of the intraoral scan, the quality control technician may highlight particular areas on the intraoral scan that need to be re-scanned. The quality control technician may also approve some or all of the information provided by the user 104 (e.g., the personal information 302, the health and consent information provided in the health and consent questionnaire, various other information such as shipping information, etc.). In implementations such as these, the quality control technician may ensure that subsequent visits to the intraoral scanning site 106 or unnecessary calls to the user 104 are avoided by collecting all necessary information during a single appointment of the user 104.

In some embodiments, following administration of the intraoral scan, the technician may take one or more photographs of the user's 104 mouth. The technician may take the photographs of the user's 104 upper and lower jaw (in some instances with a smile spreader). The technician may take a head-on photograph of the user's 104 smile. The technician may take the one or more photographs using a digital camera. Additionally or alternatively, the technician may take the one or more photographs using a camera of the user device 600. In each of these implementations, the photographs may be an initial set of photos that is used for compliance checks. The photographs may be saved to the user file 134.

Once the quality control technician approves of the intraoral scan (and photographing), the user 104 may leave the room where the user 104 received their intraoral scan. The user may go to, for instance, a waiting area or front desk area. At the front desk area, the user 104 may be shown or given various products. For instance, the user 104 may be shown what the aligners generally look like (e.g., substantially transparent, translucent, etc.). The user 104 may also be shown the packaging in which the aligners are delivered and the corresponding instruction manual. The user 104 may be provided with various dental-related items. For instance, the user 104 may be provided with lip balm, teeth whitening kits, a tote bag, etc. Each of these examples may further increase the likelihood of the user 104 purchasing aligners that are custom to the user's 104 teeth. In some embodiments, instead of receiving products at a front desk area, the user 104 may be shown or given various products in the room where they received the intraoral scan. In some embodiments, the user 104 may be shown the aligners/packaging prior to receiving the intraoral scan (e.g., at check-in), during a break, etc.

In some embodiments, the user 104 may be presented with a fast track option for generating a set of aligners from the intraoral scan. The fast track option may be a form that is filled out by the user 104, may be an oral agreement from the user, etc. The fast track option may authorize a provider of the aligners to automatically generate the aligners once the treatment plan (or the final teeth position) for the user 104 is approved by a doctor (e.g., a dentist, an orthodontist, etc.).

The user 104 may be prompted to pay at the time of the intraoral scan (or set up a payment plan at the time of the intraoral scan). Once the user 104 pays (or sets up the payment plan), the user 104 may authorize fast tracking the generation of the aligners. In implementations such as these, the user 104 may not be required to authorize the treatment plan. Rather, the treatment plan may be shown in the user portal, as will be discussed in greater detail below. Additionally, once the treatment plan is approved by the doctor, the treatment plan may be automatically used for generating the aligners and automatically uploaded to the user portal.

In some embodiments, the doctor (e.g., the dentist, orthodontist, etc.) may approve of the treatment plan following the doctor seeing the user via a video conference or a video of the user. For instance, the doctor may "see" the user remotely prior to approving the treatment plan. In still other embodiments, the doctor may approve of the treatment plan without the video conference or the video of the user. In each of these embodiments, the doctor may approve of the treatment plan for the user without having to physically see the user in person. Accordingly, the user may not be inconvenienced with a trip to a doctor's office, which may also save time for the user.

Where the user 104 does not authorize fast tracking the generation of the aligners, the user 104 may authorize the treatment plan once the treatment plan is sent to the user 104 via the user portal. Following authorization of the treatment plan, the aligners may be generated and sent to the user 104. Additionally, following authorization of the treatment plan, the user 104 may then be prompted to pay for the aligners (or sign up for a payment plan).

In some embodiments, the treatment plan may be generated by a dental professional using a computing system at a treatment plan site. The treatment plan site may be separate from the intraoral scan sites, the fabrication site, etc. In other embodiments, the treatment plan site may be the same as the intraoral scan site and/or the fabrication site. Accordingly, two or more of these sites may be consolidated into one site.

The treatment plan may be generated by manipulating individual teeth in the three-dimensional representation of the user's mouth. For instance, the dental professional may manipulate one or more teeth of the user's mouth (as represented in the three-dimensional data) from a starting position (at the time of the intraoral scan) to an ending position (following treatment). Following the teeth being moved to the ending position, the treatment plan may automatically be generated (e.g., by a computer or computing system) in accordance with a set of rules. The set of rules may include rules which constrict an amount of movement of a single tooth between two sequential aligners (for instance, 3.00 mm). Following the treatment plan being generated, various models (e.g., positive molds of the user's dentition) may be generated which correspond to the position of the teeth at various intervals between the starting and ending position. The aligners may then be generated by thermoforming a polymer material to each of the various models (with a first aligner corresponding to the starting position of the user's teeth in the user's dentition, the second [and subsequent] aligner corresponding to an intermediate position[s], and the final aligner corresponding to the final position of the user's teeth in the user's dentition).

Following generation of the aligners, all aligners associated with the treatment plan may be sent to the user 104. In some implementations, the aligners may be generated and sent to the user 104 in packaging similar to the packaging described in U.S. Patent Application Ser. No. 62/522,847, filed on Jun. 21, 2017, titled "DENTAL IMPRESSION KITS AND METHODS THEREFOR," U.S. patent application Ser. No. 15/725,430, filed on Oct. 5, 2017 and having the same title, and U.S. Patent Application Ser. No. 62/648,229, filed on Mar. 26, 2018 and having the same title, each of which are incorporated by reference in their entirety as noted herein.

Post-Appointment

Following the user 104 having their intraoral scan administered at the scan shop 106, the user 104 may receive one or more messages generated via the message generator 136. Accordingly, in some embodiments, the message generator 136 can include instructions for generating and communicating one or more messages to the user 104 following the user's 104 appointment.

In some implementations, the message generator 136 can include instructions to generate a message including various surveys and/or questionnaires. These surveys may be used for evaluating the user's 104 experience at the intraoral scanning site 106. In some implementations, the surveys may solicit the user 104 for a review on a customer review website such as Yelp®, Google®, etc. Additionally, where the user 104 receives a whitening kit at their appointment, the message generated via the message generator 136 may include whitening tips for the user 104. In each of these implementations, the messages generated via the message generator 136 may be used as feedback for subsequent user's appointments, and to enhance the experience for the user 104.

In some implementations, the message generator 136 can include instructions for generating various messages specifically when a user 104 does not attend their appointment. For instance, when the user file 134 indicates the user 104 did not show up for their appointment, the message generator 136 can include instructions for automatically generating a message including a survey for evaluating reasons why the user 104 did not showed up for their appointment. The survey generated in these implementations may solicit the user 104 to provide suggestions of what the intraoral scanning site 106 (or website) could do differently. The survey generated in these implementations may also solicit the user 104 to provide information as to how the user 104 would like to be contacted in the future (e.g., via phone call, text message, email, etc.). In some instances, the message generated via the message generator 136 may include an indication to the user 104 that the user 104 does not require an appointment for an intraoral scan and that the user can show up at an intraoral scanning site 106 any time during business hours (e.g., that walk-ins are welcome). In each of these implementations, the messages are provided to the user 104 when the messages may increase the likelihood of the user 104 scheduling or otherwise visiting the intraoral scanning site 106, and may assist in improvements to the overall experience for other users.

Additionally, where the user 104 misses their appointment, in some instances, the user 104 may be provided a free at-home impression kit (similar to those described in U.S. Patent Application Ser. No. 62/522,847 and U.S. patent application Ser. No. 15/725,430). The at-home impression kit may be sent to the user 104 via first class mail. For instance, when the user file 134 indicates the user 104 did not show up for the appointment, the message generator 136 can include instructions to automatically generate a message to the user 104 that indicates that an at-home impression kit will be sent at no charge to the user 104. Additionally, the message generator 136 can include instructions to generate a prompt that is transmitted to, for instance, a processing or shipping warehouse. The prompt may include an address or shipping label and instructions to send an at-home impression kit to the user 104 at the address.

User Portal

Figure 8:
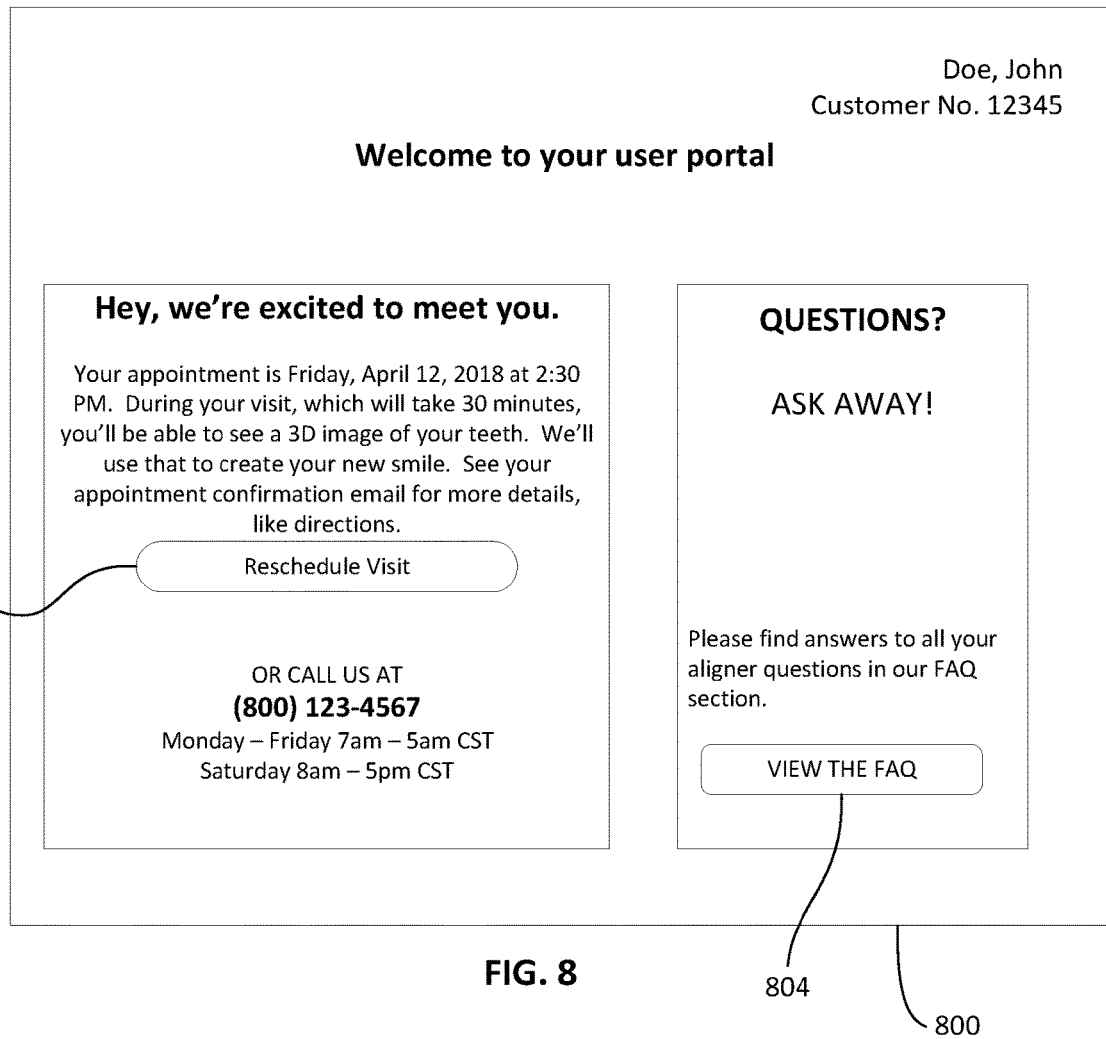
FIG. 8 is a user portal screen displayed to the user prior to the user's appointment according to an exemplary embodiment.

Referring now to FIG. 1 and FIG. 8, a user portal is generated for the user 104. Specifically shown in FIG. 8 is an example user portal 800 associated with the user 104. The example user portal 800 shown in FIG. 8 is generated prior to the user's 104 appointment. The appointment management system 100 may include a portal manager 140. The portal manager 140 may be or include instructions, that when executed by the processor 108, cause the processor 108 to generate/modify/change/manage one or more aspects of the user portal 800. As shown, the user portal 800 may include a brief overview of what to expect at the user's 104 appointment. The user portal 800 may include a button 802 to reschedule the user's 104 appointment. The button 802 may direct the user 104 to a page similar to reservation page 200. Additionally, the user portal 800 may include a button 804 to view a Frequently Asked Questions (FAQ) page providing answers to questions that the user 104 may have.

Figure 9:
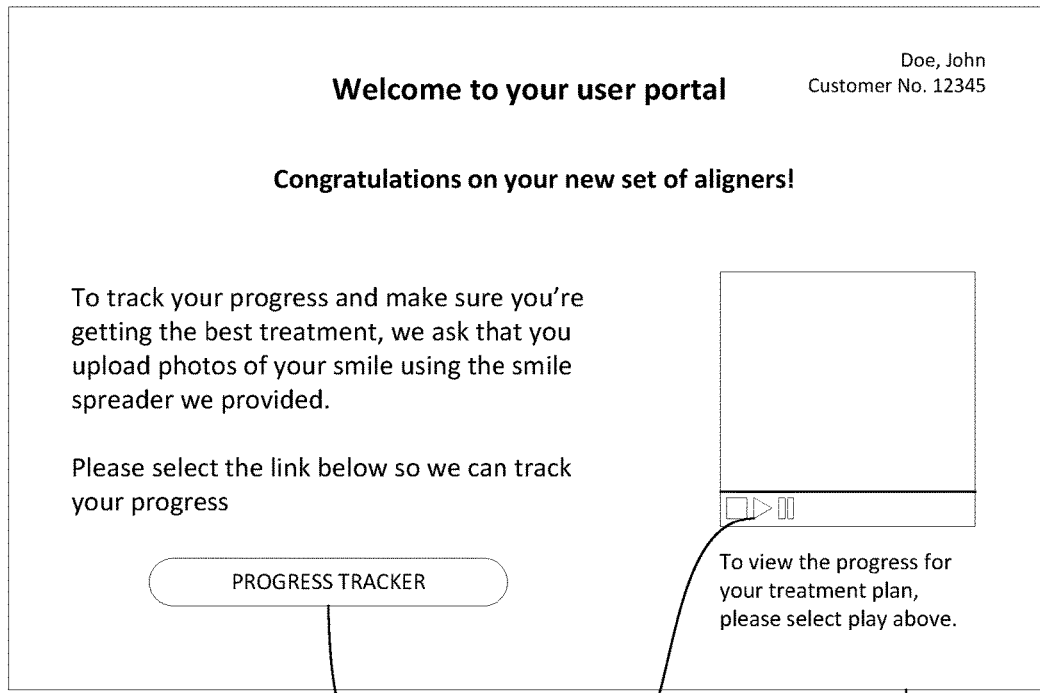
FIG. 9 is an example of a user portal screen displayed to the user following the user's appointment according to an exemplary embodiment.

Referring now to FIG. 1 and FIG. 9, the portal manager 140 may include instructions to modify the user portal 800 following the user's 104 appointment. For instance, as shown in FIG. 9, the user portal 800 is generated following the user's 104 appointment. The user portal 800 shown in FIG. 9 may include a visual representation (shown as a video) of the user's 104 treatment plan. The visual representation may show changes in the user's 104 smile as the user 104 progresses through various stages of the treatment plan. The visual representation may be a series of photos, a video, etc. The user 104 may be able to view the visual representation through selection of a button 900 (e.g., play button).

Additionally, the user 104 may be required (or requested) to provide progress information. As will be discussed in greater detail below, the progress information provided by the user 104 may be used for evaluating compliance and issuing a mid-course correction.

The user 104 may select a button 902 for providing progress information. The user 104 may be required to provide progress information at various stages along the treatment plan. For instance, the user 104 may be required to provide progress information at the outset of the treatment plan, as each aligner is used, following 90 days from the outset of the treatment plan, and/or other stages in the treatment plan. In some implementations, the appointment management system 100 may issue reminders to the user 104 for providing the progress information. For instance, the message generator 136 and/or portal manager 140 can include instructions to automatically generate one or more messages to communicate to the user 104 at various points throughout the treatment plan. As one example, when the aligners are received by the user 104 (e.g., as detected by a delivery notification), the delivery notification may be indicated in the user file 134. When the user file 134 indicates the delivery notification, the message generator 136 and/or portal manager 140 can include instructions to automatically generate one or more messages for the user 104 instructing the user 104 to provide initial progress data. When uploaded, the portal manager 140 can include instructions to store the initial progress data in the user file 134 as a baseline. The message generator 136 and/or portal manager 140 may include instructions to generate subsequent messages reminding the user 104 to upload progress data at various stages of the treatment plan, as described above. The message generator 136 and/or portal manager 140 can include instructions to identify a send date upon which the message corresponding to the initial progress data was communicated to the user 104. Additionally, the message generator 136 and/or portal manager 140 can include instructions to identify a current date. Based on a difference between the send date and the current date, the processor 108 may generate subsequent messages based on the instructions from the message generator 136 (and/or portal manager 140). Similarly, the message generator 136 and/or portal manager 140 can include instructions to generate messages directing the user 104 to change which aligners they are using (e.g., directing the user 104 to stop using a first set of aligns and to instead use a second set of aligners, directing the user 104 to stop using a third set of aligners and instead use the second set of aligners, to stop using the aligners altogether and to wait for new aligners to be sent to the user 104, etc.). Such messages may be generated similar to the messages for providing progress data.

Figure 10:
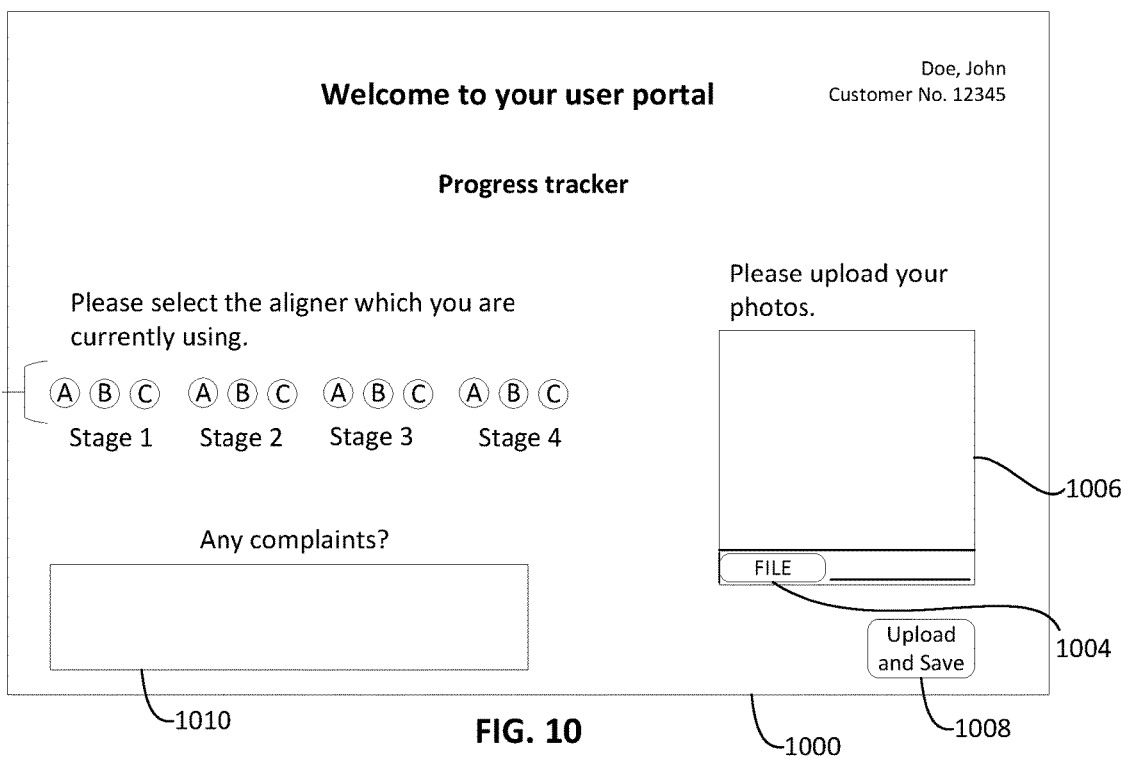
FIG. 10 is an example of a user portal screen displaying a progress tracker according to an exemplary embodiment.

Referring now to FIG. 1 and FIG. 10, upon selection of button 902, the portal manager 140 can include instructions to direct the user 104 to a progress tracker page 1000 within the user portal 800. Within the progress tracker page 1000, the user 104 is prompted to indicate which aligner the user 104 is currently using (e.g., through selection of a corresponding button 1002). Additionally, the user 104 is prompted to upload photos of the user's 104 smile. The user 104 may be instructed (e.g., either on the user portal 800, the progress tracker 1000, or separate instruction manual) on how to capture photos. For instance, the user 104 may be instructed to capture photos while using a smile spreader (e.g., a device positioned in the user's 104 mouth intended to push back the user's 104 lips and expose a greater area of the user's 104 teeth). The user 104 may be instructed to position the smile spreader in the user's 104 mouth and capture images at various angles. The user 104 may be instructed to capture an image of the user's 104 teeth head-on while biting down. The user 104 may be instructed to capture an image of the user's 104 lower jaw while opening the user's 104 mouth. The user 104 may be instructed to capture an image of the user's 104 upper jaw while opening the user's 104 mouth. The user 104 may be instructed to capture additional/alternative images of the user's 104 teeth. Each of these images may be uploaded by the user 104 using button 1004. Upon selection of button 1004, the user 104 may be prompted to search for and locate the image to upload. The image may be previewed (e.g., in display box 1006) once the user 104 locates the file. The user 104 may then select an upload button 1008 to upload the images to the user portal 800. When the images are uploaded, the portal manager 140 can include instructions to automatically add these images to the user file 134.

The user 104 may provide comments regarding the progress or fit of the aligners in comments box 1010. For instance, the user 104 may indicate that the user 104 is not satisfied with the progress of realigning the user's 104 teeth or how the user's 104 smile looks. As another example, the user 104 may indicate that the aligners do not fit or are uncomfortable. Each of these indications may indicate that the user 104 may require a mid-course correction. As used herein, a mid-course correction is defined as a new treatment plan developed for the user 104 following an indication that the current treatment plan is no longer desirable for the user 104. Accordingly, the user 104 receives a new intraoral scan, a new set of aligners, etc. In this regard, no cross-reference is made between the first treatment plan and the second treatment plan. However, in some implementations, the mid-course correction comprises receipt of at least one new set of aligners, which may be created for the user 104 following new intraoral scan or new impressions to be made of the user's 104 teeth. In some implementations, the mid-course correction may be free to the user 104. For instance, as discussed below, the mid-course correction may be free following a compliance check indicating that the user 104 is correctly following the treatment plan.

The compliance check may be a review of the progress data provided by the user (e.g., via progress tracker 1000). In some implementations, following the user 104 uploading any comments via comments box 1010, the portal manager 140 may include instructions to automatically flag the user file 134 and communicate the file to a professional terminal 142. The professional terminal 142 may be a computer associated with one or more professionals (e.g., doctors, dentists, orthodontists, etc.). The professional terminal 142 may display the user file 134 including the images uploaded by the user 104 and the current aligner which is being used by the user 104. The user file 134 may be evaluated by the professionals to determine whether the user 104 is progressing according to the treatment plan, whether the user 104 is following the treatment plan as instructed, etc. Where the user 104 is not following the treatment plan as instructed, the user file 134 may be flagged as not being in compliance. Where the user 104 is following the treatment plan but is not progressing according to the treatment plan, portal manager 140 may flag the user file 134 for a mid-course correction. Where the user file 134 is flagged as not being in compliance, the user 104 may be required to pay for the mid-course correction. However, where the user 104 is following the treatment plan, the mid-course correction may be offered to the user 104 for free.

In some implementations, when the user 104 is following the treatment plan as instructed and progresses through the treatment plan, the message generator 136 and/or portal manager 140 may include instructions to automatically generate a message (and corresponding flag in the user file 134) indicating that the user 104 is eligible for a free dental check-up and cleaning at a dental clinic or associated dental office.

Mobile Dentition Scanning

Figure 11:
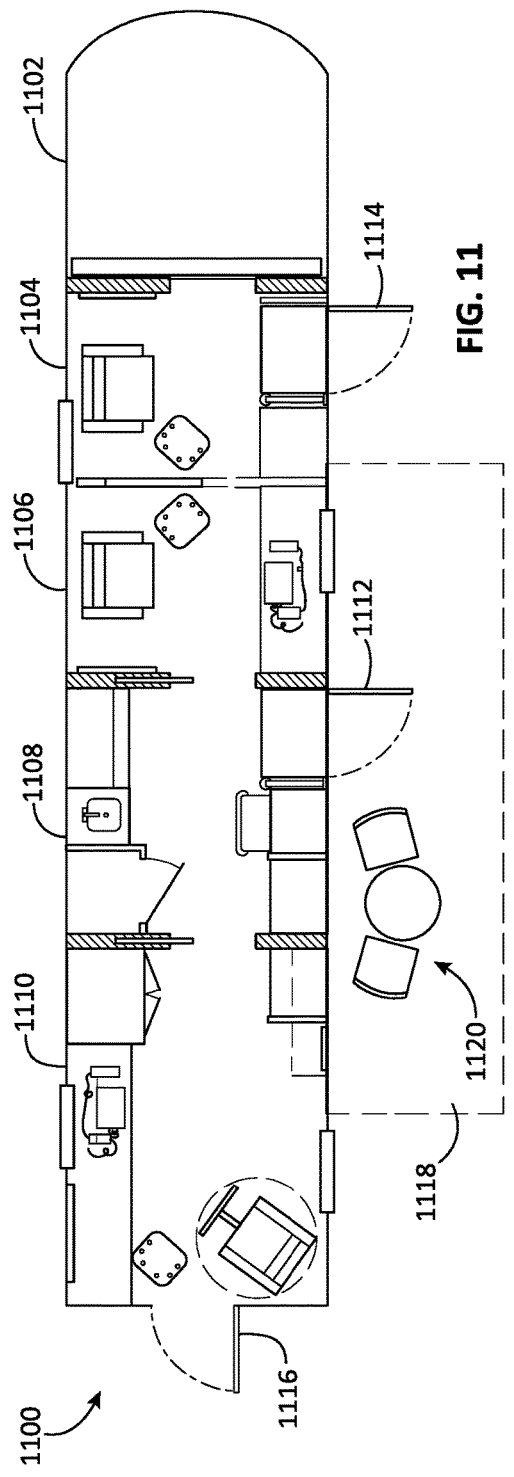
FIG. 11 is a top-down schematic view of a mobile intraoral scanning site, according to an exemplary embodiment.
Figure 12:
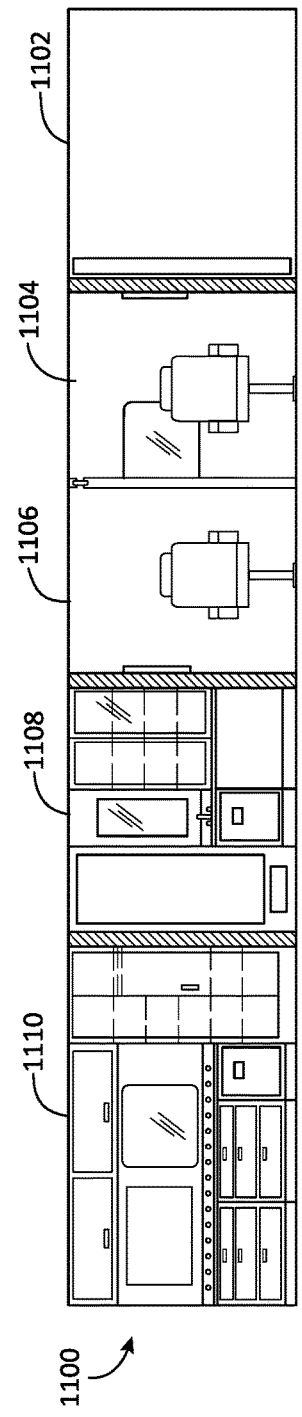
FIG. 12 is a first side view of the mobile intraoral scanning site of FIG. 11, according to an exemplary embodiment.
Figure 13:
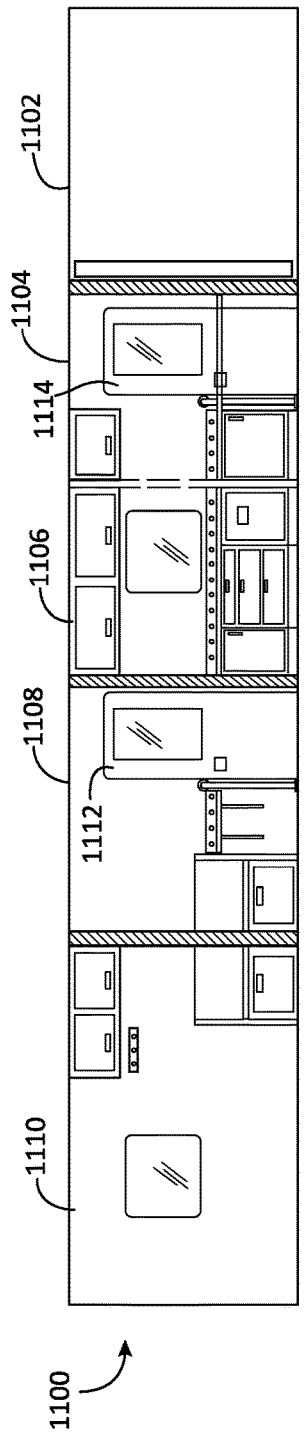
FIG. 13 is a second side view of the mobile intraoral scanning site of FIG. 11, according to an exemplary embodiment.

As indicated above, in some embodiments, one or more of the intraoral scanning sites 106 may be a mobile intraoral scanning site 106. For example, a mobile intraoral scanning site 106 may be implemented as a vehicle, such as a bus. FIGS. 11, 12, and 13 illustrate a mobile intraoral scanning vehicle 1100, according to exemplary embodiments. FIG. 11 shows a top-down schematic view of the intraoral scanning vehicle 1100, FIG. 12 shows a first side view of the intraoral scanning vehicle 1100, and FIG. 13 shows a second side view (from the opposite side) of the intraoral scanning vehicle 1100. As shown in FIGS. 11-13, the vehicle 1100 contains various compartments. The front compartment in the vehicle 1100 is a driver's cabin 1102. The driver's cabin 1102 leads into a first scan station 1104 (e.g., with a privacy curtain separating the driver's cabin 1102 from the first scan station 1104). The first scan station 1104 is adjacent to a second scan station 1106 (e.g., with a sliding partition wall separating the first scan station 1104 from the second scan station 1106). The second scan station 1106 is next to a reception area 1108. At the back of the vehicle 1100 is a third scan station 1110. Each of the second scan station 1106 and the third scan station 1110 is separated from the reception area 1108 by a sliding door.

The vehicle 1100 include multiple entrances, shown as doors, for entering and exiting the vehicle 1100. For example, as shown in FIGS. 11 and 13, the vehicle 1100 may include a main door 1112 leading into the reception area 1108, as well as a secondary door 1114 leading into the first scan station 1104. The vehicle 1100 may also include a back door 1116 leading into the third scan station 1110 (e.g., for emergency or disabled entry and exit from the vehicle 1100). In some embodiments, the vehicle 1100 also includes an awning 1118 that can be extended from or retracted into the side of the vehicle 1100. For example, as shown in FIG. 11, the awning 1118 may be extended to create a greeting area 1120 for welcoming individuals seeking to have a dentition scan taken at the vehicle 1100. The greeting area 1120 may be further created by, as an illustration, setting up tables and chairs stored under the vehicle 1100 for creating a check in area for users.

The various compartments of the vehicle 1100 may be outfitted with hardware for facilitating the use of the vehicle in performing intraoral scanning for various users. As an illustration, each of the scan stations 1104, 1106, and 1110 may include a chair for the user receiving the intraoral scan to sit in during the scan. The scan stations 1104, 1106, and 1110 may further include a stool for the staff member performing the intraoral scan to use, a guest bench, a wall-mounted television, a wall-mounted intraoral scanner, coat hooks, etc. Similarly, the reception area 1108 may include a guest bench or one or more guest chairs, a chair, a desk, a sink and mirror, a fridge, etc. The scan stations 1104, 1106, and 1110 and the reception area 1108 may further include storage, such as cabinets, drawers, closets, and wardrobes, for storing the supplies for performing intraoral scans and other related supplies (e.g., reference manuals) when not in use. For example, cabinets in the second scan station 1106 and the third scan station 1110 may store wall-mounted 3D scanners when not in use or when the vehicle 1100 is traveling (e.g., in protective pelican cases).

Figure 14:
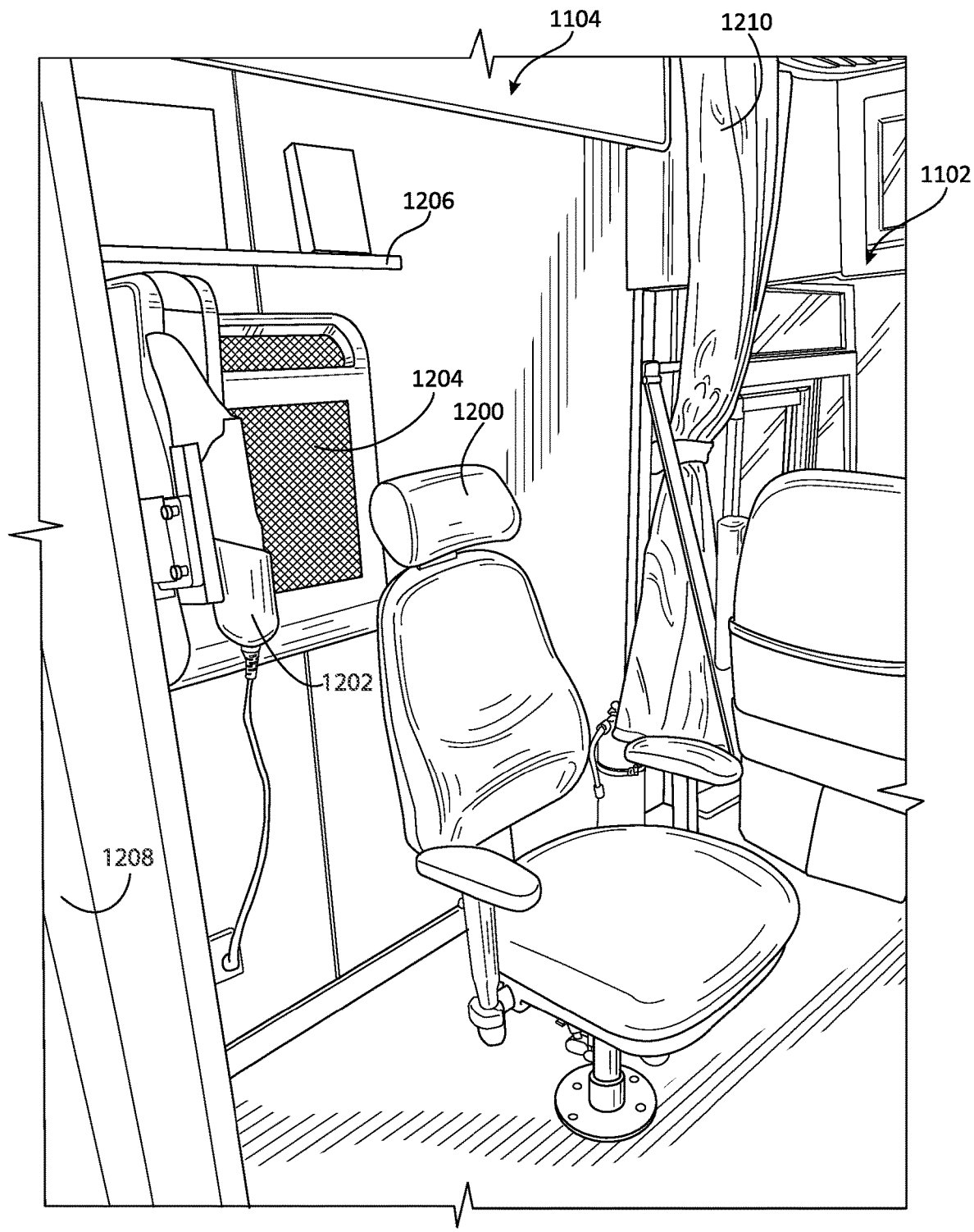
FIG. 14 is a first view of a scan station of a mobile intraoral scanning site, according to an exemplary embodiment.

FIGS. 14-17 illustrate views of the interior of the vehicle 1100, according to exemplary embodiments. Referring first to FIG. 14, an exemplary view of the interior of the first scan station 1104 is shown (e.g., facing the driver side of the vehicle 1100). The first scan station 1104 includes a chair 1200 (e.g., a fixed captain's chair) for the user to sit in while the intraoral scan is performed and a wall-mounted intraoral scanner 1202 for performing the scan. The first scan station 1104 also includes a window 1204 and shelving 1206. The first scan station 1104 is separated from the second scan station 1106 by a sliding partition wall 1208 (partially shown) and separated from the driver's cabin 1102 by a privacy curtain 1210.

Figure 15:
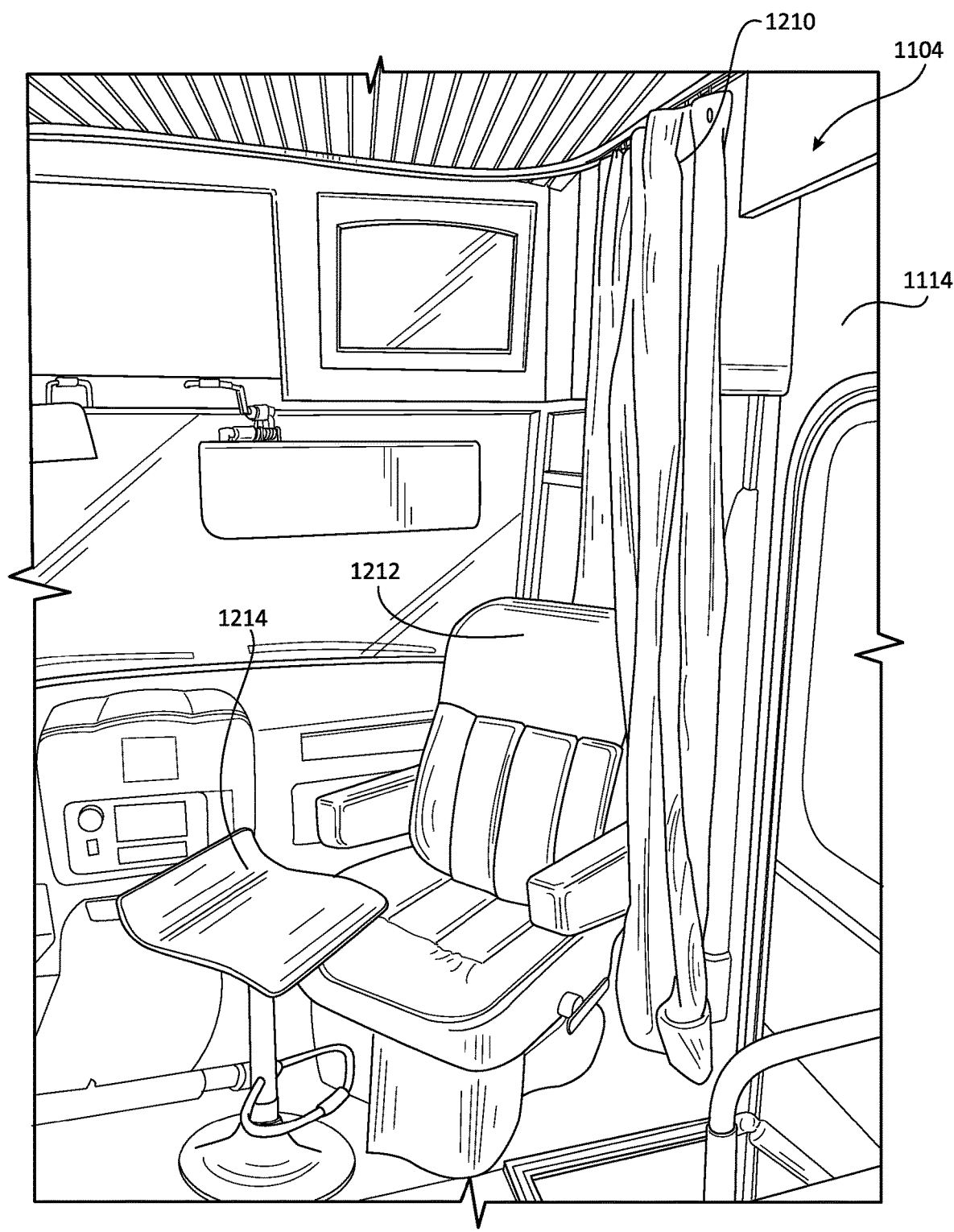
FIG. 15 is a second view of the scan station of FIG. 14, according to an exemplary embodiment.

Referring now to FIG. 15, another exemplary view of the interior of the first scan station 1104 is shown (e.g., facing the passenger side of the vehicle 1100). As shown in FIG. 15, the first scan station 1104 further includes a passenger seat 1212 that can be turned around to provide guest seating in the first scan station 1104, as well as a stool 1214. Individuals can enter and exit the first scan station 1104 through the secondary door. Additionally, FIG. 15 illustrates another privacy curtain 1210 that can be used to separate the first scan station 1104 from the driver's cabin 1102.

Figure 16:
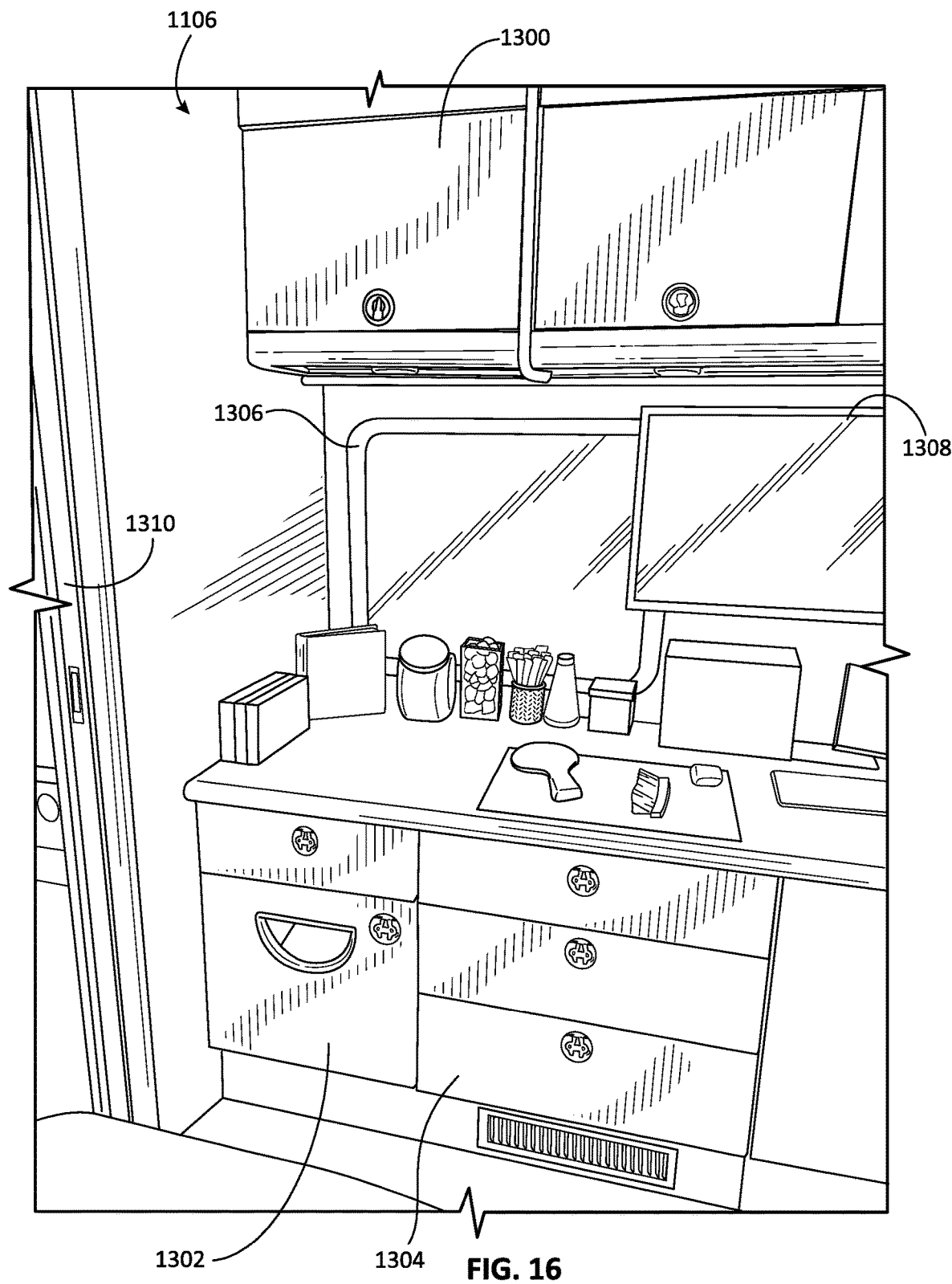
FIG. 16 is a view of a second scan station of a mobile intraoral scanning site, according to an exemplary embodiment.

Referring now to FIG. 16, an exemplary view of the interior of the second scan station 1106 is shown. In addition to a chair and wall-mounted intraoral scanner as in the first scan station 1104 (not shown), the second scan station 1106 includes overhead cabinets 1300, lower cabinets 1302, and drawers 1304 for storing supplies for performing the intraoral scans and other supplies, such as pens and lip balm to provide to users. The second scan station 1106 also includes a window 1306 and a wall-mounted television 1308. Further, the second scan station 1106 is separated from the reception area 1108 by a sliding door 1310 (e.g., a sliding frosted acrylic door).

Figure 17:
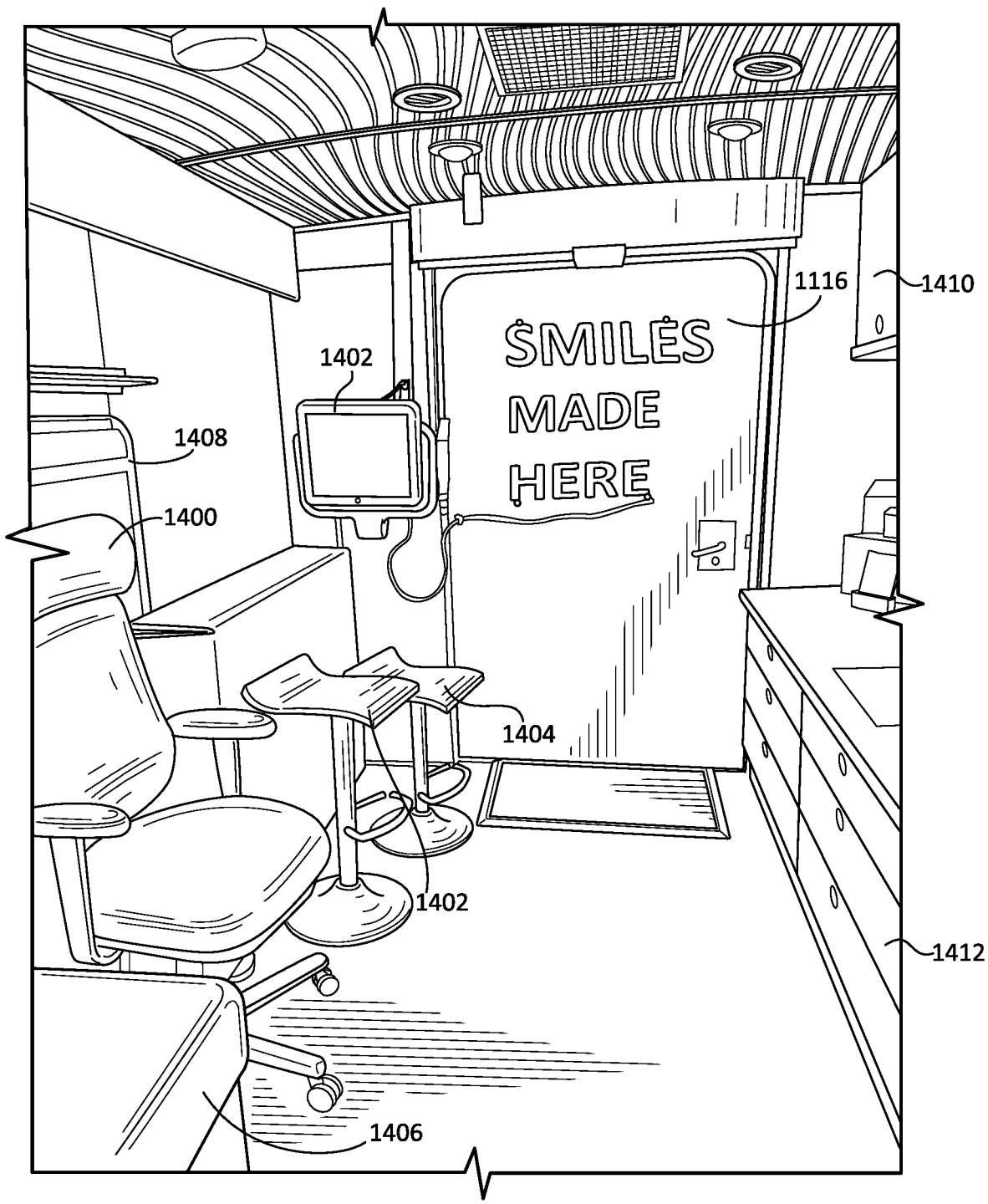
FIG. 17 is a view of a third scan station of a mobile intraoral scanning site, according to an exemplary embodiment.

Referring now to FIG. 17, an exemplary view of the interior of the third scan station 1110 is shown. The third scan station 1110 includes a chair 1400 (e.g., a salon chair) for the user to sit in while the intraoral scan is performed, a wall-mounted intraoral scanner 1402, and stools 1404. The third scan station 1110 also includes a guest bench 1406 for guests of the users to sit on while the intraoral scan is taken. The third scan station 1110 further includes a window 1408, as well as overhead cabinets 1410 and drawers 1412 for storage. As discussed above, the third scan station 1110 additionally includes the back door 1116 used, for example, for emergencies and/or for disabled access to the third scan station 1110.

It should be understood that the vehicle 1100 is exemplary and that other configurations of a vehicle 1100 used as a mobile intraoral scanning site 106 are contemplated herein. For example, a vehicle 1100 may include one compartments, two compartments, or more than three compartments for conducting intraoral scans. Furthermore, any type of vehicle may be used in place of vehicle 1100, such as a bus, a Recreational Vehicle, a vehicle towing a trailer, or a van, among others.

In some embodiments, the vehicle 1100 may be custom-built to be the mobile intraoral scanning site 106. In other embodiments, the vehicle 1100 may be retrofitted to be the mobile intraoral scanning site 106. For example, the vehicle 1100 may be a commercial Winnebago® that is modified to include, for example, fixed captain's chairs, a passenger seat that rotates as shown in FIG. 15 to serve as guest seating, the secondary door 1114, overhead and lower cabinets and drawers, cabinet lighting, undercarriage lighting, external speakers, and so on. In various arrangements, the electronic items on the vehicle (e.g., the wall-mounted 3D scanners, wall-mounted televisions, fridge, etc.) may be powered with a generator, such as a gas-fueled generator, or by a back-up battery.

As an illustration of the use of the vehicle 1100 for performing intraoral scanning of various users, a user may be checked in by staff at the greeting area 1120 (e.g., using the check-in process described above). Alternatively, if weather is poor such that the greeting area 1120 cannot be set up (e.g., it is too windy to release the awning 1118), the user may be checked in by staff in the reception area 1108. The user may wait in the reception area 1108 or outside the vehicle 1100 (e.g., in the greeting area 1120) until the user's scan can be performed. For example, the user may wait until it is time for the user's appointment, or the user may wait until one of the scan stations 1104, 1106, and 1110 is available for a walk-in appointment. The user is then guided to one of the scan stations 1104, 1106, and 1110. For example, if the user's scan is to be performed in the second scan station 1106 or the third scan station 1110, a staff member may guide the user from the reception area 1108 through a sliding door into the adjacent scan station 1106 or 1110. If the user's scan is to be performed in the first scan station 1104, a staff member may guide the user from the reception area 1108 through a sliding door into the second scan station 1106 and then through a sliding partition into the first scan station 1104. Alternatively, if the second scan station 1106 is in use, the staff member may guide the user out the main door 1112 and through the secondary door 1114 into the first scan station 1104 (e.g., to ensure the privacy of a user having an intraoral scan performed in the second scan station 1106). A staff member then performs the intraoral scan of the user's dentition using an intraoral scanner (e.g., a wall-mounted intraoral scanner or a mobile intraoral scanner stored in cabinets of the vehicle), using the processes described above. A staff member may also take pictures of the user's teeth, for example, while the user is biting or while the user has their mouth open. After the intraoral scan has been performed, the user can then leave the vehicle 1100, and the post-scanning process described above is applied to the user's situation.

In various embodiments, feedback may be solicited from a user once the user's scan is completed at the vehicle 1100. For example, a staff member at the vehicle 1100 may ask the user directly how the user's experience at the vehicle 1100 was or ask the user to fill out a survey before leaving the vehicle 1100. As another example, the message generator 136 may generate a message for the user asking the user to provide feedback or fill out a survey on the user's experience with the vehicle 1100, which the notification center 138 sends to the user. In some embodiments, this feedback may be stored in the memory 110 and used to refine the process for providing scans at the vehicle 1100, for generating locations for the vehicle 1100, and so on in the future. To illustrate, the computing system 102 may compile the feedback into a list for an employee to review or may automatically analyze the feedback to identify the most common complaints for the employee to review. In some arrangements, the feedback may also include feedback from staff members working on the vehicle 1100 and/or statistics on the vehicle 1100 event at the location. These statistics may include how many users visited the vehicle, what the weather was like, how many intraoral scans were performed, how many users decided to purchase aligners after receiving the intraoral scan, how many users decided to preauthorize the purchase of aligners, how many five star reviews the users left on social media after visiting the vehicle 1100 (e.g., after receiving a text message created by the message generator 136 prompting the user to leave a review), and so on.

The vehicle 1100 further includes an internet connection (e.g., via the communications device 114) such that each intraoral scan taken on the vehicle 1100 can be uploaded to a central location, such as a central server or a cloud server. For example, the internet connection may be provided by a cellular network, with the vehicle 1100 including one or more antennas (e.g., eight or nine antennas on the top of the vehicle 1100) and/or one or more subscriber identification module ("SIM") cards for facilitating the connection to the cellular network. The intraoral scanners may then connect via Wi-Fi or an Ethernet connection on the vehicle 1100 such that the intraoral scanners can upload the scans via the connection and the cellular network. Additionally, the vehicle 1100 may also be provided with one or more mobile devices (e.g., tablet computers) that can be used to take pictures of users' teeth and also upload the pictures to a cloud server via the internet connection.

In various embodiments, determining the schedule for the vehicle 1100, including the locations to which the vehicle 1100 will travel and/or how long the vehicle 1100 will be positioned in those locations, may occur according to a combination of variables associated with a likelihood of individuals scheduling intraoral scanning appointments and/or with navigating the vehicle 1100. These variables may include time of year (e.g., prioritizing traveling to colder climates during the summer and warmer climates during the winter), population density (e.g., prioritizing traveling to more dense population centers), income (e.g., prioritizing traveling to areas with higher average incomes), zip code (e.g., prioritizing traveling to zip codes with higher average incomes), age (e.g., prioritizing traveling to areas with higher numbers of individuals within a certain age range, such as 30-45), distance from a stationary intraoral scanning site 106 (e.g., maintaining the location of the vehicle within a hard or soft distance, such as 20 miles, from any stationary intraoral scanning sites 106), and history of past locations visited (e.g., prioritizing traveling to areas that have not been visited by a vehicle 1100). In some embodiments, the variables may be weighted when determining the location for the vehicle 1100 to travel. For example, income and zip code may be weighted the most heavily, with time of year, distance from a stationary intraoral scanning site 106, and history of past locations visited having a secondary weighting and the remaining variables having a tertiary weighting.

As an illustration of selecting a location for the vehicle 1100, between Area A, having an average income of $100,000 per year but with a lower population density, and Area B, having an average income of $80,000 per year with a higher population density, Area A may be selected. As another illustration, between Area C, having an average income of $100,000 per year located in Minnesota, and Area D, having an average income of $95,000 per year located in Georgia, Area D may be selected during the winter and Area C may be selected during the summer. In some embodiments, the vehicle 1100 may be one of a number of vehicles 1100, with each vehicle 1100 assigned to a particular geographic region. As an example, for vehicles 1100 within the United States, the vehicles 1100 may be assigned to one of East Coast, West, North Central, Southeast, South Central, Northwest, Texas, California, and Florida. Accordingly, the variables may include keeping the vehicle 1100 within or near the assigned geographic region.

Additionally, in some embodiments, the general locations for the vehicle 1100 may include locations where a stationary intraoral scan station 106 may be located in the future, where a stationary intraoral scan station 106 is in the process of being built, desirable areas (e.g., based on the number of visitors to a website associated with the vehicle 1100 that are from the given area) that are too small to support their own stationary intraoral scan station 106, and/or areas where it would be desirable to raise brand awareness through a visit by the vehicle 1100. Similarly, in some embodiments, the general locations for the vehicle 1100 may be based at least partially on locations where potential users have shown interest in completing intraoral scans and purchasing aligners. For example, the general locations may be at least partially based on the number of visitors to a website associated with the vehicle 1100 (e.g., discussing or advertising the process of aligning teeth with aligners) from a given area based on IP addresses and/or location information provided by the visitors. As another example, the general locations may be at least partially based on the number of users who have performed one or more actions suggesting that they would like to purchase aligners (e.g., booked an intraoral scan at a stationary intraoral scanning site 106 but missed the appointment or not purchased aligners afterwards). As an illustration, the number of visitors to the website associated with the vehicle 1100 having IP addresses within an area, the number of visitors to the website who provided location information (e.g., a zip code) located within the area, and the number of visitors to the website who performed one or more actions on the website and who are located within the area (e.g., based on a zip code provided by the visitor or the IP address of the visitor) may all be used as additional variables in determining the general location. For instance, between Area A, having an average income of $90,000 per year, and Area B, having $85,000 per year but encompassing a larger number of visitors to the website, Area B may be selected.

Once a general location (e.g., a city, a zip code) is selected, a specific location for the vehicle 1100 is determined. For example, areas with large parking lots, such as malls, within the general location may be identified as potential specific locations for the vehicle 1100. One or more variables may also factor into determining the specific location, such as accessibility and distance from stationary intraoral scanning sites 106. With the specific location for the vehicle 1100 determined, the best route for the vehicle 1100 to travel from its current location to the specific location is identified. As an example, the best route may take into account road inclines, road declines, locations of freeways or highways, fuel capacity and gas station locations, and so on. Additionally, the itinerary for the vehicle 1100 (as well as staffers working on the vehicle 1100) may be uploaded to a cloud database such that the itinerary can be accessed by other employees associated with the vehicle 1100.

Figure 18:
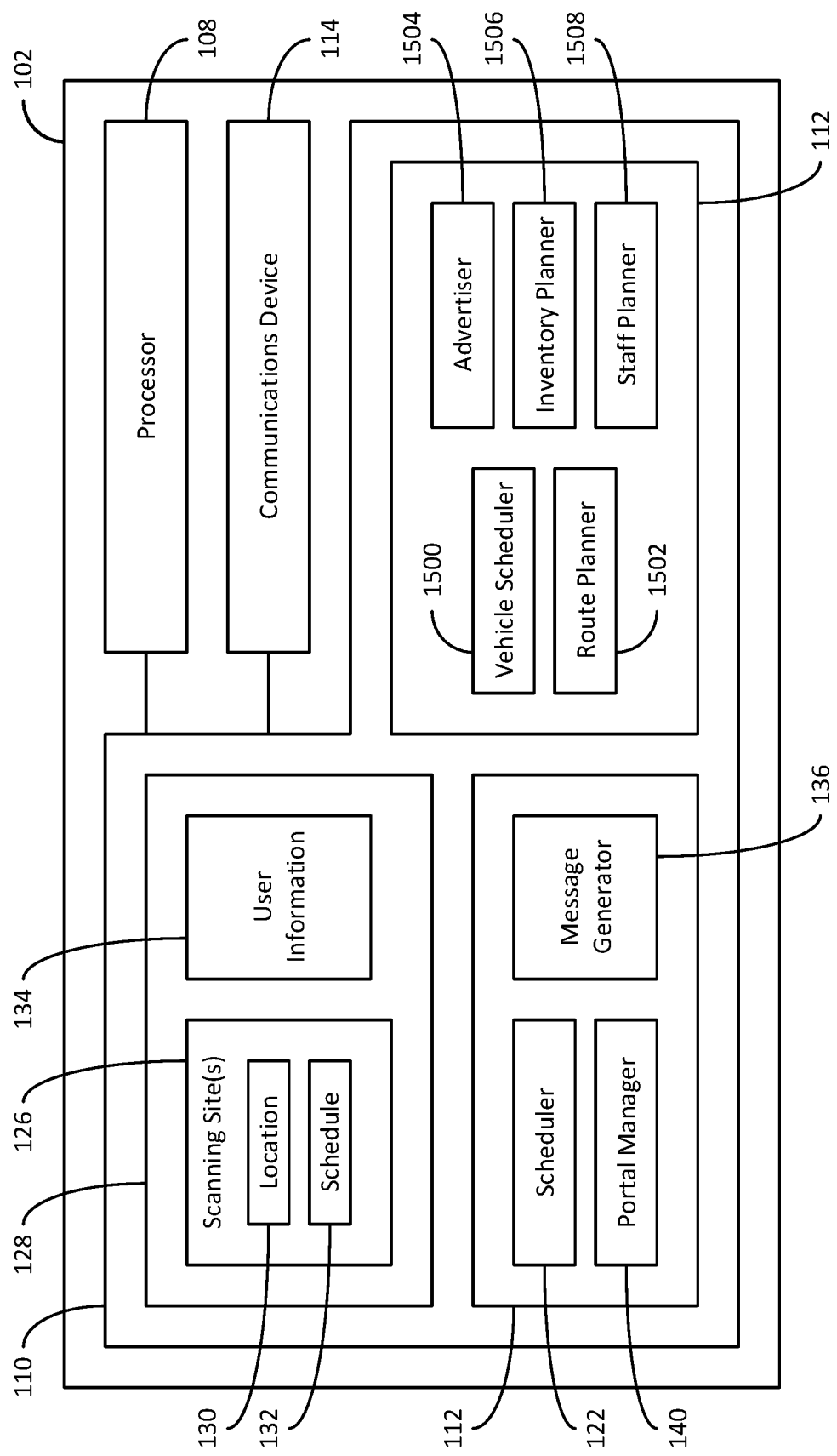
FIG. 18 is a portion of the appointment management system of FIG. 1 for scheduling appointments for a mobile intraoral scanning site, according to another exemplary embodiment.

In various arrangements, some or all of these determinations may be made automatically by a computing system. As an illustration, FIG. 18 shows another embodiment of the computing system 102. As shown in FIG. 18, the memory 110 of the computing system may include a circuit 112 including a vehicle scheduler 1500, a route planner 1502, an advertiser 1504, an inventory planner 1506, and a staff planner 1508. The vehicle scheduler 1500 may be configured to evaluate potential general and specific locations for the vehicle 1100 based on the one or more variables and identify the optimal general and/or specific locations. In one example, the vehicle scheduler 1500 may identify various potential general locations (e.g., with the potential general location being a metropolitan area, a zip code, a neighborhood, etc.) and assign scores to the potential general locations based on their fit with the one or more variables and factors discussed above. The vehicle scheduler 1500 may determine that the potential general location with the highest score should be used as the next general location in the schedule for the vehicle 1100. The vehicle scheduler 1500 may further run a similar analysis to determine a specific location for the vehicle 1100.

In another example, the vehicle scheduler 1500 may output a list of potential general locations (e.g., listed in an order based on their score from the one or more variables and factors discussed above) to a staff member associated with the computing system 102. The staff member then uses the list to determine specific locations for the vehicle 1100, for example, by contacting properties with locations large enough to house the vehicle 1100 (e.g., malls with large parking lots) to gain approval for the vehicle to be stationed at the specific location, as well as any additional legwork such as filing for approval with the local municipality to use the specific location. In another example, at least some of the legwork may be performed automatically by the vehicle scheduler 1500 (e.g., with the vehicle scheduler 1500 automatically identifying and contacting the owner of the specific location to gain approval).

Additionally, the route planner 1502 may be configured to determine the route for the vehicle 1100 once the schedule for the vehicle 1100 is determined (e.g., by the scheduler 1500). As an example, the route planner 1502 may use a mapping application to determine the shortest route between the vehicle's current location and the next location in the schedule, modifying the route as needed to account for the need to refill gas, avoid construction, avoid steep hills, and the like.

In various embodiments, once the schedule for the vehicle 1100 is determined, advertising may be used to indicate the availability of the vehicle 1100 in the given area for the period of time on the schedule to various potential users. For example, in some arrangements, advertising may be used on a social media platform according to geofencing to identify potential users within a certain distance of the scheduled location of the vehicle 1100 (e.g., based on information input by the user into the social media platform, based on the user's location determined by the social media platform from the user's IP address, based on the user's location determined by an application associated with the social media platform running on a mobile device associated with the user from a global positioning system ("GPS") on the mobile device). The social media platform may then provide advertisements to potential users on the social media platform who are within the geofence (e.g., a forty mile radius from the scheduled stop of the vehicle 1100 or a smaller radius if there is a nearby stationary intraoral scanning station 106). As an example, the advertisements may start three days before a scheduled stop of the vehicle 1100 and continue until the day before the last day of the scheduled stop. The advertisements may also be tailored to certain demographics (e.g., individuals 18-65). Further, in certain arrangements, additional factors may be used to advertise to potential users on the social media platform who are more likely to schedule an appointment with the vehicle 1100, such as potential users within the geofence that the social media platform has determined are above a certain income level or that the social media platform has determined have similar demographics to others that have clicked on the advertisement in the past. In some embodiments, the advertiser 1504 may interface with the social media platform (e.g., using an application programming interface ("API") of the social media platform) to automatically initiate targeted advertising to potential users on the social media platform once the schedule of the vehicle 1100 is determined.

The advertisements used on the social media platforms may be tailored to the specific stop location. As an illustration, an advertisement may list the location, the dates that the vehicle 1100 will be stopped at the location, and illustrate the urgency of the individual needing to book an intraoral scan at the location due to the limited timeframe of the stop and limited number of available scanning appointments. Additionally, the advertisement may be configured to link directly to the intraoral scan booking page (e.g., the reservation page 200).

In some embodiments, the advertiser 1504 may also vary the budget for advertisements used, for example, on social media platforms based on the number of available intraoral scanning appointments over time. As an example, a vehicle 1100 may have a total of 72 intraoral scanning appointments available per day. The advertiser 1504 may determine the number or percentage of open appointments over time (e.g., based on information from the scheduler 122) and increase or decrease the budget based on how that number/percentage compares to an average or expected number/percentage given the timing relative to the scheduled stop.

Further advertising may be carried out by social media accounts associated with the vehicle 1100. For example, the schedule of the vehicle 1100 may be posted on a Twitter® account and/or an Instagram® account associated with the vehicle 1100 (e.g., the upcoming schedule for the post may be posted every Monday). In some arrangements, this may be performed directly by the advertiser 1504 (e.g., by using one or more application programming interfaces ("APIs") to post the schedule once determined by the scheduler 1500).

In some arrangements, the computing system 102 may directly carry out at least some of the advertising based on contact information for various potential users (e.g., stored in the user file 134). For example, a user making an appointment using the reservation page 200 may be required to input both location information (e.g., the city and zip code in which the user lives) and contact information (e.g., a mobile phone number and/or an email address). As such, the computing system 102 may store the location information and contact information in the user file 134. As another example, a user may by prompted to input location information and contact information when visiting a website associated with the vehicle 1100 (e.g., a website discussing or advertising the process of aligning teeth with aligners), which is stored in the user file 134. Alternatively, the location information may be determined based on the user's IP address used to access the website. As another example, the computing system 102 may receive location information and contact information for potential users of desired demographics from a marketing list that is stored in the user file 134. As yet another example, employees associated with the computing system 102 may receive location information and contact information for potential users through in-person advertising, which they input into the user file 134.

Once the schedule of the vehicle 1100 is set, the message generator 136 may identify, based on the user file 134, users in the geofences associated with upcoming locations for the vehicle 1100 that should be contacted. These users may include, for example, users that scheduled but missed intraoral scan appointments, users that completed an intraoral scan but did not purchase aligners afterwards, users that indicated they would like to learn more about the process of receiving aligners, users in desired demographics, and so on. A given geofence used may be a certain distance from a scheduled stop of the vehicle 1100, such as within a forty-mile radius of the scheduled stop. The message generator 136 may generate messages for these users indicating when the vehicle 1100 will be in the upcoming location within their respective geofences and directing the users to make an appointment with the vehicle 1100. For example, the messages may be emailed or texted to the users, with the messages including a link that the users can select to make an appointment with the vehicle 1100 (e.g., directing the user to the reservation page 200). As another example, the messages provided by an automatic call to the users, with the automatic call including instructions for making an appointment with the vehicle 1100 (e.g., instructions for accessing the reservations page). The notification center 138 may then provide the messages to the users. However, for users that book an intraoral scanning appointment with the vehicle 1100, the message generator 136 may remove those users from the messaging list such that they do not receive unnecessary messages.

Additionally, in some arrangements, multiple types of communications may be sent to the potential users. For instance, an email communication may be sent to users in a geofence (e.g., within a forty mile radius of a scheduled stop) five days before a scheduled stop of the vehicle 1100. In addition, a text message may be sent to users in the same geofence or a narrower geofence two days (e.g., within a ten mile radius of the scheduled stop) before the scheduled stop of the vehicle 1100. Additionally, once the user books an intraoral scan with the vehicle 1100, the message generator 136 may generate an email message and a text message for the user confirming the appointment date and time, as well as including instructions for finding the location of the vehicle 1100 at the scheduled stop.

In some arrangements, the messages may include a sense of urgency for the potential users. For example, a first email communication may be sent out to the users in a geofence five days before the scheduled stop of the vehicle 1100. After that, email communications may be sent at regular times until the end of the scheduled stop of the vehicle 1100 to indicate the short timeframe of the vehicle 1100 stop, such as a reminder email communication indicating that the user can still book an intraoral scan at the time the scheduled stop begins and a last change communication the day before the last day of the scheduled stop. The email communications may also clearly state the limited time that the vehicle 1100 will be at the scheduled stop and emphasize the number of open intraoral scan appointments left, as well as indicate the limited dates and location in the subject line.

Additionally, in some arrangements, the messages may be tailored to the individual user, for example, based on the user's familiarity with the aligner process. As an illustration, a first message may be sent to users who have never made an appointment for an intraoral scan. A second message may be sent to users who have made but missed an appointment for an intraoral scan. A third message may be sent to users who have previously purchased an impression kit used to make impressions of the user's teeth (e.g., instead of the user having an intraoral scan performed). A fourth message may be sent to users that received a scan at a stationary intraoral scan station 106 but did not purchase aligners. Finally, a fifth message may be sent to users that received a scan at a stationary intraoral scan station 106 or previously used and sent in an impression kit but need a redo scan (e.g., because it has been a certain amount of time since the first scan, because there were issues with the image file for the first scan, because the dental impression the user took with the dental impression kit was not clear enough). As another illustration, different messages may be sent to different users based on their demographics (e.g., different messages based on age).

Figure 19:
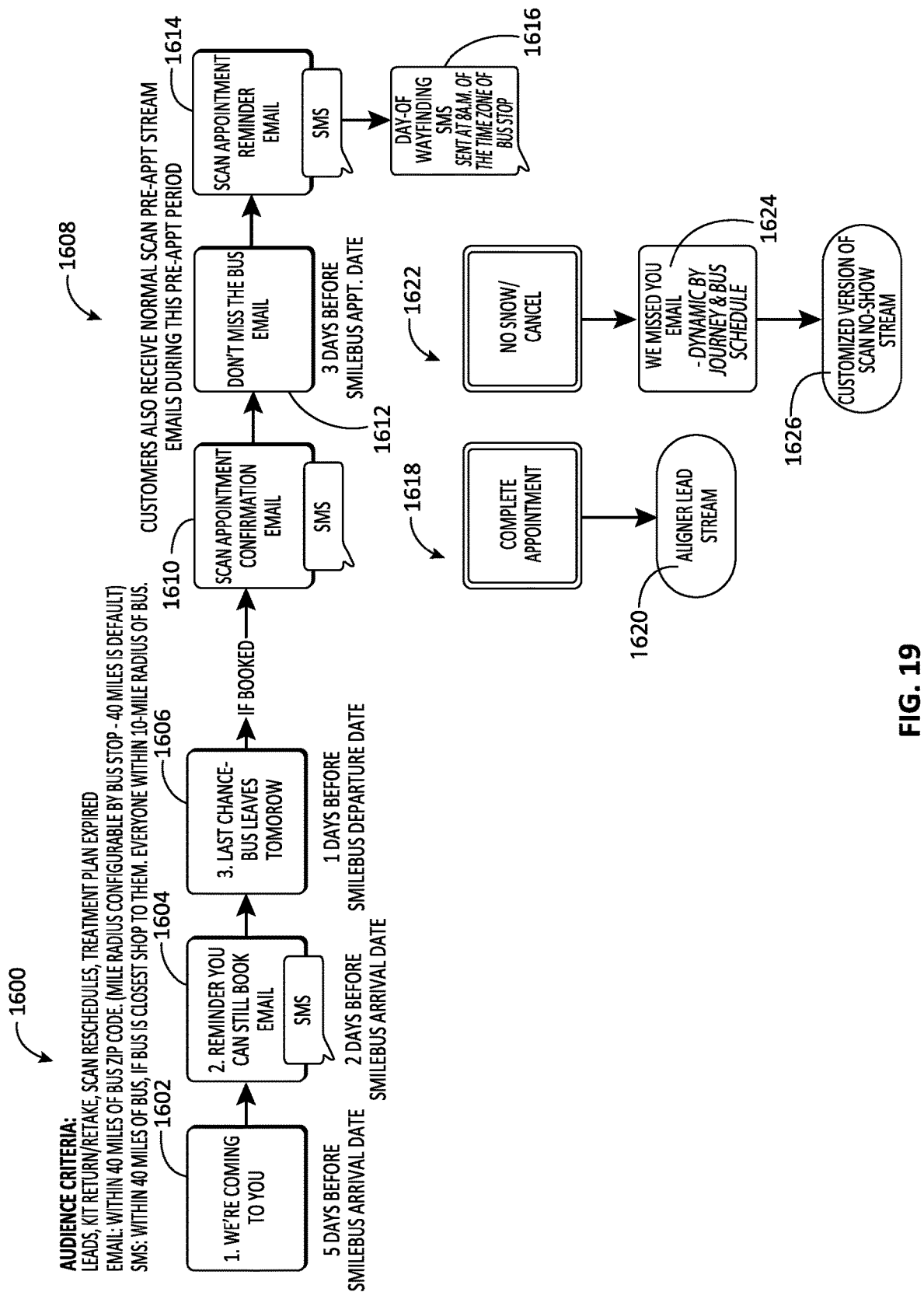
FIG. 19 is a flow diagram of a messaging process associated with a mobile intraoral scanning site, according to an exemplary embodiment.

FIG. 19 illustrates the types of messages the message generator 136 may create for a user. Specifically, the messages shown in FIG. 19 are tailored to users saved in the user file 134 as leads (e.g., users potentially interested in purchasing aligners), users needing to return an impression kit, users needing to retake an intraoral scan or dental impression created using an impression kit, users needing to reschedule an intraoral scan, and users who had a treatment plan created at one time that is now expired (e.g., due to the user not purchasing aligners within a certain amount of time after the treatment plan was created). Group 1600 includes three sets of messages sent before the user books an intraoral scan with the vehicle 1100. Message 1602 includes an email sent to the users five days before the vehicle 1100 arrives indicating that the vehicle 1100 is coming to a location near the user. Message 1604 includes an email and a text message reminding the user that the user can still book an intraoral scan at the vehicle 1100. The email and text message are sent two days before the vehicle 1100 is scheduled to arrive at the location near the user. Message 1606 includes an email sent one day before the vehicle 1100 is scheduled to depart the location and indicates that this is the user's last chance to book an intraoral scan because the vehicle 1100 leaves the next day.

Group 1608 includes messages sent to the user after the user has booked an intraoral scan with the vehicle 1100. For example, at the point the user books the intraoral scan, the user stops receiving the group 1600 messages and starts receiving the group 1608 messages. Message 1610 includes an email and a text message confirming that the user has booked an intraoral scan appointment. Message 1612 includes an email sent three days before the user's intraoral scan appointment reminding the user of the appointment. Message 1614 includes another email and a text message reminding the user of the appointment, and message 1616, which is sent the day of the appointment (e.g., at 8 AM local time), includes a text message instructing the user on how to find the location of the vehicle 1100. In addition to receiving the group 1608 messages, the user may also receive messages that are typical for users to receive before an intraoral scan at an intraoral scanning site 106, as discussed above.

If the user completes the intraoral scanning appointment, the user receives the group 1618 message. Specifically, the user receives one or more messages 1620 instructing the user on the next steps for purchasing and receiving aligners. If the user misses or cancels the intraoral scanning appointment, the user receives the group 1622 messages. Message 1624 includes an email indicating that the user missed the appointment and providing the upcoming schedule of the vehicle 1100 to the user. Additionally, the user receives one or more messages 1626 providing the user with additional information on aligners and/or what steps the user should take if the user decides to purchase aligners in the future.

In various embodiments, scheduling appointments for intraoral scans at the vehicle 1100 is done using a similar process as for other intraoral scanning sites 106. In some arrangements, the user may schedule a scanning appointment at the vehicle 1100 using the reservation page 200 of the website associated with the appointment management system 100. As an illustration, once the schedule of locations, dates, and times the vehicle 1100 will be available for performing intraoral scans is determined, the vehicle 1100 may be selectable in the locations 202, dates 204, and times 206 of the reservation page 200 for those determined locations, dates, and times. For example, the vehicle 1100 may be selectable on the reservation page 200 starting seven days before the vehicle 1100 is scheduled to arrive at the location. Accordingly, a user can schedule a scanning appointment with the vehicle 1100 using the process described above with respect to the reservation page 200. The reservation page 200 may be populated with those locations 202, dates 204, and times 206 in a similar manner as described above, with the scheduler 122 accessing the schedule 124 of the vehicle 1100 acting as the intraoral scanning site 106. To ensure that the upcoming schedule for a vehicle 1100 appears on the reservation page 200, for example, the vehicle scheduler 1500 may create a ticket for the scheduler 122 confirming the days the vehicle 1100 will be at a given stop, the hours of operation at the stop, the number of available chairs per appointment time at the given stop, and so on.

Additionally, in various embodiments, the user may receive pre-appointment messaging and/or post-appointment messaging as described above. For example, in some embodiments, the message generator 136 may generate messages for users scheduled for appointments with the vehicle 1100 instructing the user how to get to the vehicle 1100 location. The messages may be automatically generated by the message generator 136 (e.g., using a mapping application) or may be input manually by a staff member working on the vehicle 1100.

Because the vehicle 1100 is a mobile intraoral scanning site 106, certain steps may also be taken to ensure that the vehicle 1100 remains stocked with supplies for performing the intraoral scans, as well as other supplies for the intraoral scanning site 106. For example, staffers working on the vehicle 1100 may count inventory levels at the beginning of a vehicle 1100 stop at the scheduled location and the end of the stop at the scheduled location or at the end of each day the vehicle 1100 is stopped at the scheduled location. The county of the inventory levels may be provided to a central database (e.g., a database incorporated as part of or communicably connected to the inventory planner 1506). As an example, the inventory levels may be provided to a shared document in the central database, which automatically tracks the inventory of supplies at each vehicle 1100. In some arrangements, the shared document may alert an employee when inventory levels are low at a vehicle (e.g., by flagging the inventory as red in the document, by sending the employee an email), such as less than five hundred, so that the employee can order additional inventory. In other arrangements, the inventory planner 1506 may automatically track the inventory at each vehicle 1100 based on the inventory counts and automatically order additional supplies for a vehicle 1100 in response to determining that inventory is low.

In some embodiments, once the vehicle 1100 is low on stock, a shipment of supplies may be sent to a hotel at which staffers working on the vehicle 1100 are staying. In other embodiments, once the vehicle 1100 is low on stock (e.g., as recorded and reported by staff working on the vehicle 1100), a shipment of supplies may be sent to the nearest current or upcoming stationary intraoral scanning site 106 such that the vehicle 1100 can pick up the supplies at the stationary intraoral scanning site 106.

In some embodiments, the vehicle 1100 may be staffed with individuals who work on the vehicle 1100 full-time. For example, the staffers may travel with the vehicle 1100, or the staffers may divided into two groups that alternate between working the vehicle 1100 at scheduled stops. In other embodiments, the vehicle 1100 may be staffed with local individuals. As an example, staffers (e.g., one manager and four to five scanning associates) working at stationary intraoral scanning sites 106 near upcoming stops scheduled for the vehicle 1100 may travel to the location of the vehicle 1100 to staff the vehicle 1100. In various arrangements, the staff planner 1508 may determine the number of individuals needed to staff the vehicle 1100 (e.g., based on the vehicle 1100 schedule) and identify individuals able to staff the vehicle 1100. As an illustration, the staff planner 1508 may automatically identify staffers working at a stationary intraoral scanning site 106 near a scheduled stop with high reviews and contact those staffers to work at the vehicle 1100 while the vehicle 1100 is at the scheduled stop. The staff planner 1508 may further automatically determine a schedule for the staffers.

In various embodiments, providing one or more mobile intraoral scanning sites 106 in addition to stationary intraoral scanning sites 106 as described above may provide a number of advantages over using only stationary intraoral scanning sites 106. For one, the mobile intraoral scanning sites 106 may allow intraoral scans to be performed in areas that are not large enough or would likely not create enough business to sustain a stationary intraoral scanning site 106. The mobile intraoral scanning sites 106 may also allow intraoral scans to be performed in areas in which a stationary intraoral scanning site 106 is being built but is not completed. Additionally, the limited nature of the mobile intraoral scanning sites 106 providing intraoral scans may attract users who would otherwise forego getting a scan done (e.g., due to a fear of missing out). As an example, in some cases, more users may sign up to have an intraoral scan performed at a vehicle 1100 and actually follow through with the scan than at a stationary intraoral scanning site 106 within the same time period due to the transience of the vehicle 1100.

Additionally, using a mobile intraoral scanning site 106 (e.g., implemented as the vehicle 1100) may be advantageous over other implementations of remote intraoral scanning performed outside of a stationary site, such as having an employee bring an intraoral scanner into a user's home to perform the intraoral dentition scan. For example, having a dedicated vehicle 1100 configured for performing intraoral dentition scans alleviates the difficulty of an employee delivering and properly setting up the highly technical intraoral scanning equipment in a user's home. Further, as discussed above, a large number of users can schedule appointments at the vehicle 1100 for a given day that the vehicle 1100 is stationed in a location (e.g., due to the efficiency and multiple scanning stations of the vehicle 1100), whereas the number of users who can schedule appointments with an employee bringing the intraoral scanner to the users' homes is more limited (e.g., due to the travel time of the employee providing the intraoral scanner). Likewise, the geographic range that can be served by an employee bringing the intraoral scanner to the user's home may be more limited due to the employee's need to travel to the user's home from a base location, such as the employee's home or a stationary intraoral scanning site. Users may also be inconvenienced by having the intraoral scanning equipment brought to their homes, as well as be uncomfortable with inviting an employee that they do not know into their homes for security, privacy, or other reasons. By contrast, users visiting the vehicle 1100 can have an intraoral dentition scan performed at a location near the user without worrying about the inconvenience and potential security, privacy, etc. concerns of inviting an unknown individual into their homes.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media may be any available media that may be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision step.

What is claimed is:

1. A mobile intraoral scanning site, comprising:
   a vehicle;
   a communications device provided on the vehicle; and
   one or more three-dimensional intraoral scanners provided on the vehicle and configured to perform intraoral dentition scans of users on the vehicle, and configured to connect by a wireless or wired connection on the vehicle with the communications device;
   wherein the vehicle includes at least two compartments configured to be used as scan stations for performing the intraoral dentition scans of users on the vehicle, at least one of the at least two compartments is separable from an adjacent driver's cabin within the vehicle, and
   wherein a fixed chair within the at least one of the at least two compartments is a passenger chair of the vehicle located in the driver's cabin; and
   wherein the vehicle is provided with an internet connection via the communications device such that the intraoral dentition scans are first sent from the one or more three-dimensional intraoral scanners over the wireless or wired connection on the vehicle to the communications device on the vehicle before being uploaded via the communications device to a cloud server via the internet connection for generation of treatment plans without a dentist or an orthodontist having seen the users in person, and wherein a dentist or an orthodontist approves the treatment plans without having seen the users in person.

2. The mobile intraoral scanning site of claim 1, wherein the vehicle includes a reception compartment separating the two scan station compartments.

3. The mobile intraoral scanning site of claim 1, wherein at least one of the scan station compartments includes a fixed chair configured to be used by a user during an intraoral dentition scan.

4. The mobile intraoral scanning site of claim 1, wherein at least one compartment includes a disability access entrance.

5. The mobile intraoral scanning site of claim 1, wherein the vehicle is retrofitted to be used for the mobile intraoral scanning site.

6. The mobile intraoral scanning site of claim 1, wherein the one or more three-dimensional intraoral scanners are at least partially wall-mounted on the vehicle.

7. The mobile intraoral scanning site of claim 1, wherein the internet connection is provided by a cellular network.

8. A method for intraoral dentition scanning, comprising:
   providing a mobile intraoral scanning site comprising a vehicle and one or more three-dimensional intraoral scanners provided on the vehicle, wherein the vehicle includes at least two separable compartments, wherein each compartment is configured to be used as a scan station for performing intraoral dentition scans, and a communications device;
   wherein at least one of the at least two separable compartments is separable from an adjacent driver's cabin within the vehicle, and
   wherein a fixed chair within the at least one of the at least two separable compartments is a passenger chair of the vehicle located in the driver's cabin;
   performing, by the one or more three-dimensional intraoral scanners, one or more intraoral dentition scans on one or more users on the vehicle;
   uploading the one or more intraoral dentition scans to a cloud server via the communications device; and
   causing generation of one or more treatment plans using the one or more intraoral dentition scans without a dentist or an orthodontist having seen the one or more users in person, and wherein a dentist or an orthodontist approves the one or more treatment plans without having seen the one or more users in person.

9. The method of claim 8, wherein the vehicle includes a reception compartment separating the two scan station compartments.

10. The method of claim 8, wherein at least one of the scan station compartments includes a fixed chair configured to be used by a user during an intraoral dentition scan.

11. The method of claim 8, wherein at least one compartment includes a disability access entrance.

12. The method of claim 8, wherein the vehicle is retrofitted to be used for the mobile intraoral scanning site.

13. The method of claim 8, wherein the one or more three-dimensional intraoral scanners are at least partially wall-mounted on the vehicle.

14. The method of claim 8, further comprising:
   providing an internet connection on the vehicle by a cellular network.

15. The method of claim 8, further comprising sending messages associated with the mobile intraoral scanning site to a plurality of individuals, the messages inviting the plurality of individuals to schedule an appointment to receive an intraoral dentition scan at the vehicle.

16. The method of claim 8, further comprising determining a site to locate the vehicle at for a limited period of time, wherein the determination is based on a plurality of variables.

17. A method for intraoral dentition scanning, comprising:
   providing a mobile intraoral scanning site comprising a vehicle and one or more three-dimensional intraoral scanners provided on the vehicle, wherein the vehicle includes at least two compartments, each configured to be used as a scan station for performing intraoral dentition scans, and a reception area separating two compartments of the at least two compartments;
   wherein at least one of the at least two compartments is separable from an adjacent driver's cabin within the vehicle, and wherein a fixed chair within the at least one of the at least two compartments is a passenger chair of the vehicle located in the driver's cabin;
   locating the vehicle at a site for a limited period of time; and
   sending messages associated with the mobile intraoral scanning site to a plurality of individuals, the messages inviting the plurality of individuals to schedule an appointment to receive an intraoral dentition scan at the vehicle;

wherein the intraoral dentition scans are performed on the vehicle without a dentist or an orthodontist being present on the vehicle, wherein the intraoral dentition scans are used to generate treatment plans for a subset of the plurality of individuals without a dentist or orthodontist having seen any of the subset of the plurality of individuals in person, and wherein a dentist or an orthodontist approves the treatment plans without having seen any of the subset of the plurality of individuals in person.

18. The method of claim 17, further comprising performing, by the one or more three-dimensional intraoral scanners, one or more intraoral dentition scans on one or more users on the vehicle.

19. The method of claim 17, wherein the vehicle is retrofitted to be used for the mobile intraoral scanning site.

20. The method of claim 17, further comprising determining the site to locate the vehicle at for the limited period of time, wherein the determination is based on a plurality of variables.

21. The method of claim 17, wherein the at least two compartments comprises a first compartment and a second compartment, wherein the vehicle further comprises a first entrance and a second entrance, and wherein the first entrance leads to the first compartment and the second entrance leads to the second compartment.

* * * * *